United States Patent
Waki

(10) Patent No.: US 9,161,736 B2
(45) Date of Patent: Oct. 20, 2015

(54) ULTRASONIC DIAGNOSTIC APPARATUS AND ELASTICITY IMAGE DISPLAY METHOD

(75) Inventor: Koji Waki, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 499 days.

(21) Appl. No.: 13/392,652

(22) PCT Filed: Sep. 9, 2010

(86) PCT No.: PCT/JP2010/065486
§ 371 (c)(1),
(2), (4) Date: Feb. 27, 2012

(87) PCT Pub. No.: WO2011/030812
PCT Pub. Date: Mar. 17, 2011

(65) Prior Publication Data
US 2012/0157831 A1   Jun. 21, 2012

(30) Foreign Application Priority Data

Sep. 10, 2009   (JP) ................................ 2009-209837

(51) Int. Cl.
*A61B 5/05*   (2006.01)
*A61B 8/08*   (2006.01)
(Continued)

(52) U.S. Cl.
CPC . *A61B 8/08* (2013.01); *A61B 8/485* (2013.01); *G01S 7/52042* (2013.01); *G01S 7/52071* (2013.01); *A61B 8/466* (2013.01); *A61B 8/483* (2013.01); *G01S 15/8934* (2013.01)

(58) Field of Classification Search
CPC ......... A61B 8/485; A61B 8/00; A61B 5/0053
USPC ......................................... 600/427, 407, 437
See application file for complete search history.

(56) References Cited

U.S. PATENT DOCUMENTS 4,913,158 A * 4/1990 Kikuchi et al. ............... 600/446
6,270,459 B1 * 8/2001 Konofagou et al. .......... 600/449
(Continued)

FOREIGN PATENT DOCUMENTS

CN        1980606 A      6/2007
CN      101060813 A     10/2007
(Continued)

OTHER PUBLICATIONS

Nakagawa et al (Imaging of cross-sectional elasticity in short axis plane of arterial wall by transcutaneos ultrasound, 2004).*
(Continued)

*Primary Examiner* — Tse Chen
*Assistant Examiner* — Joel F Brutus
(74) *Attorney, Agent, or Firm* — Oliff PLC

(57) ABSTRACT

Disclosed is an ultrasonic diagnostic apparatus provided with: an ultrasonic probe which transmits/receives ultrasonic waves to/from an object while being in contact with the object; a transmission/reception unit which, in a process in which pressing force applied to the object by the ultrasonic probe is changed and the tomographic position at which the ultrasonic waves are transmitted/received to/from the object is moved in a short axis direction, periodically transmits/receives the ultrasonic waves to/from the object, performs reception processing on a reflection echo signal from the object, and measures RF signal frame data at the tomographic position; a displacement measurement unit which, on the basis of two pieces of RF signal frame data, between which the difference in measurement time falls within a set range, selected from among multiple pieces of RF signal frame data sequentially measured by the transmission/reception unit, finds the displacement of a living tissue at the tomographic position and sequentially generates displacement frame data; an elasticity information calculation unit which on the basis of the displacement frame data sequentially generated by the displacement measurement unit, finds elasticity information relating to the living tissue at the tomographic position, and sequentially generates elasticity frame data; and an elasticity image construction unit which on the basis of the elasticity frame data sequentially generated by the elasticity information calculation unit, sequentially constructs elasticity images.

15 Claims, 13 Drawing Sheets

(51) Int. Cl.
*G01S 7/52* (2006.01)
*G01S 15/89* (2006.01)
*A61B 8/00* (2006.01)

(56) References Cited

U.S. PATENT DOCUMENTS

| | | |
|---|---|---|
| 2004/0210137 A1* | 10/2004 | Baba et al. ............... 600/443 |
| 2006/0058649 A1* | 3/2006 | Tamano et al. ........... 600/437 |
| 2006/0241424 A1* | 10/2006 | Akiyama et al. ......... 600/437 |
| 2007/0032726 A1* | 2/2007 | Osaka et al. ............. 600/459 |
| 2007/0232916 A1* | 10/2007 | Waki ........................ 600/444 |
| 2008/0071174 A1* | 3/2008 | Waki et al. ............... 600/442 |
| 2008/0194966 A1* | 8/2008 | Kang, II ................... 600/459 |
| 2008/0269606 A1 | 10/2008 | Matsumura |
| 2009/0124903 A1 | 5/2009 | Osaka |

FOREIGN PATENT DOCUMENTS

| | | |
|---|---|---|
| JP | A-2000-060853 | 2/2000 |
| JP | A-2006-271523 | 10/2006 |
| JP | A-2008-237664 | 10/2008 |
| JP | A-2008-259555 | 10/2008 |
| JP | A-2008-259605 | 10/2008 |
| WO | WO 2005/120358 A1 | 12/2005 |
| WO | WO 2006/054635 A1 | 5/2006 |

OTHER PUBLICATIONS

International Search Report issued in Application No. PCT/JP2010/065486; Dated Oct. 5, 2010 (With Translation).
Chinese Office Action issued in Application No. 201080040183.X; Dated Aug. 22, 2013 (With Translation).
Japanese Office Action issued in Application No. JP 2011-530864, dated Jun. 4, 2014 (with English language Summary).

\* cited by examiner

FIG. 3
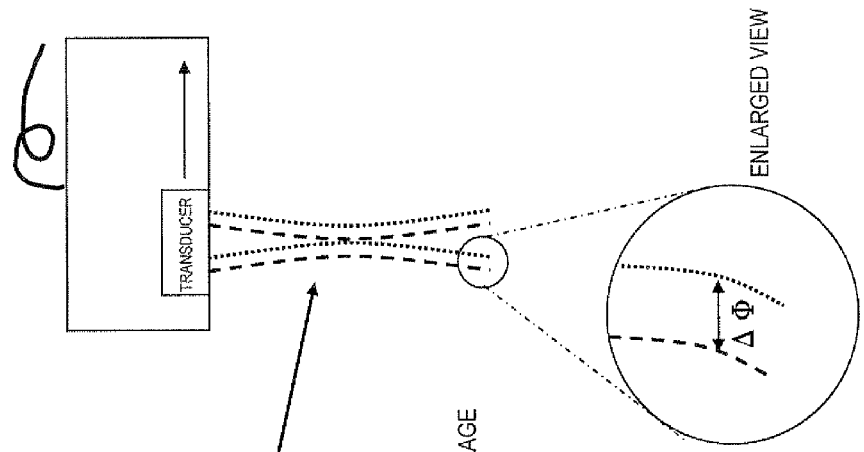
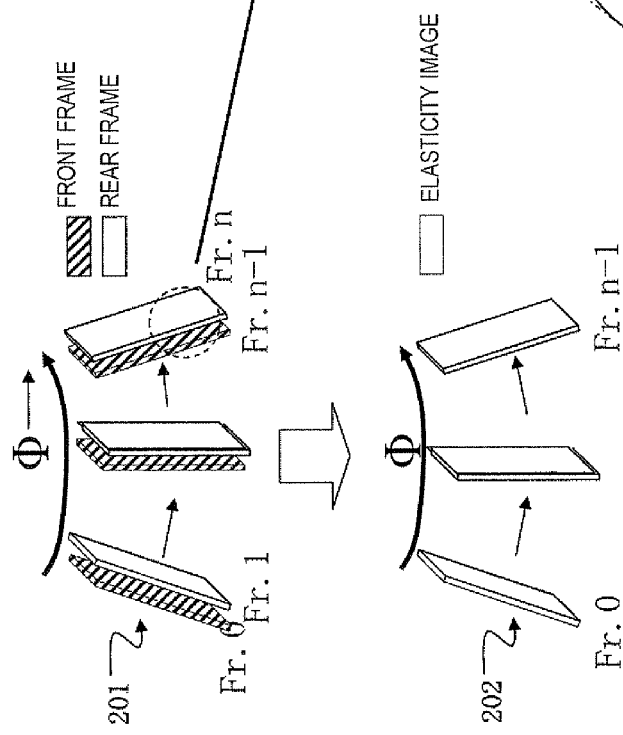

FIG. 4
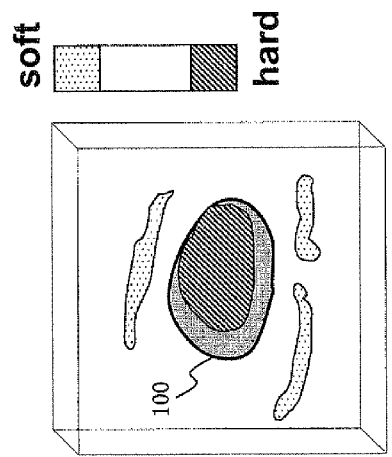
(b)
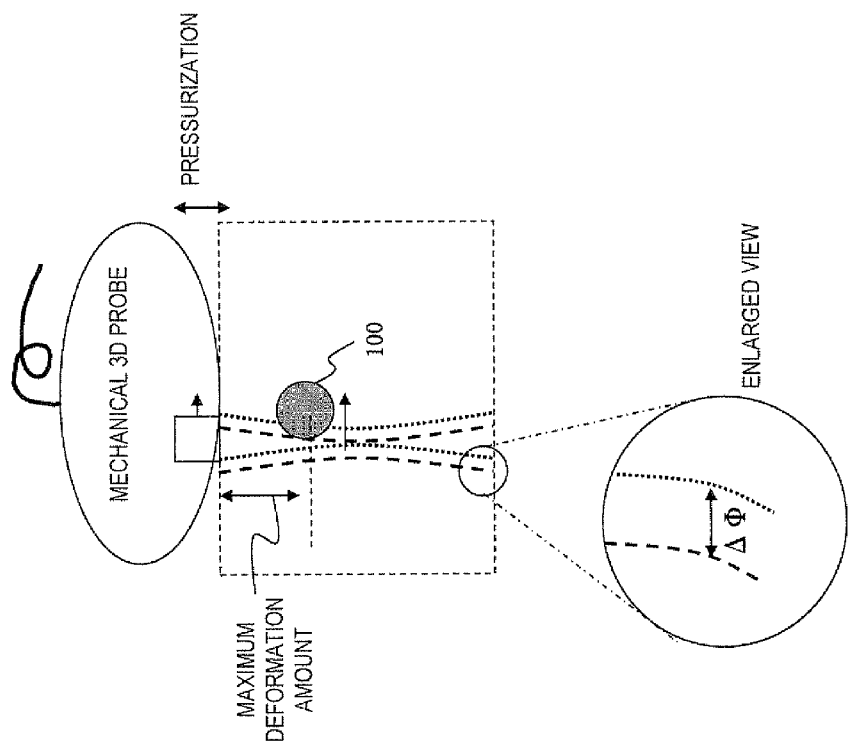
(a)

FIG. 5
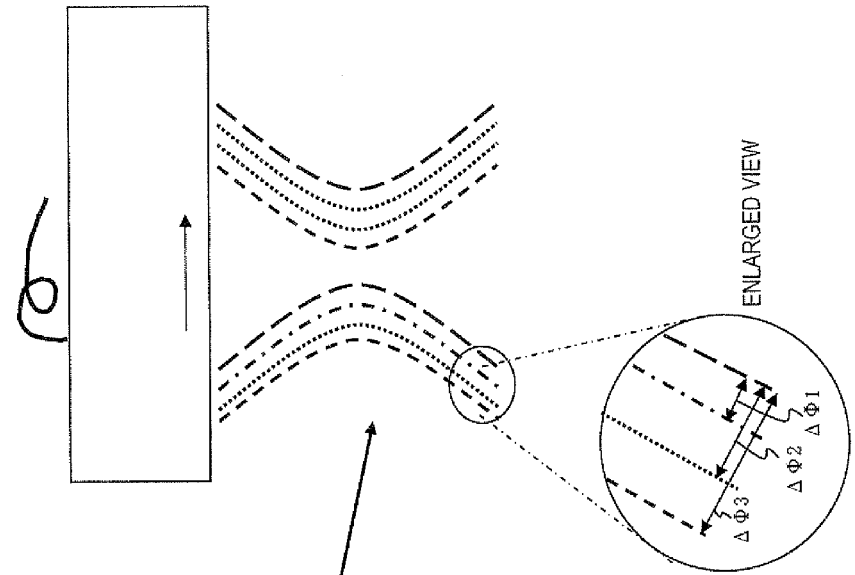
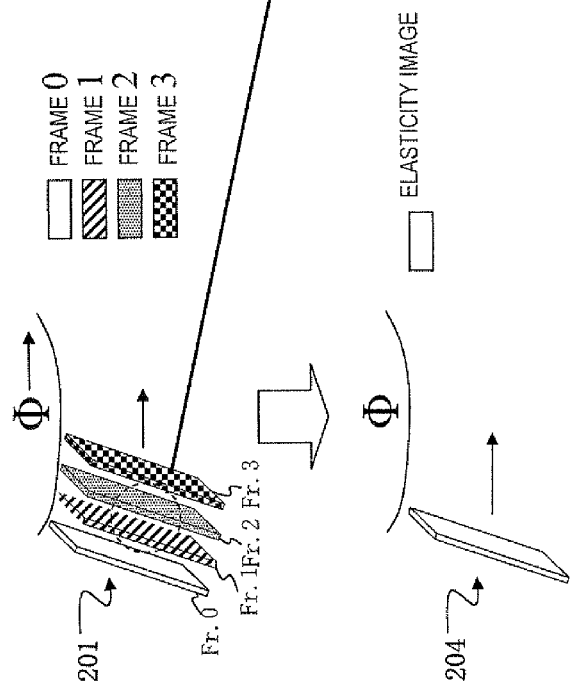

FIG. 6
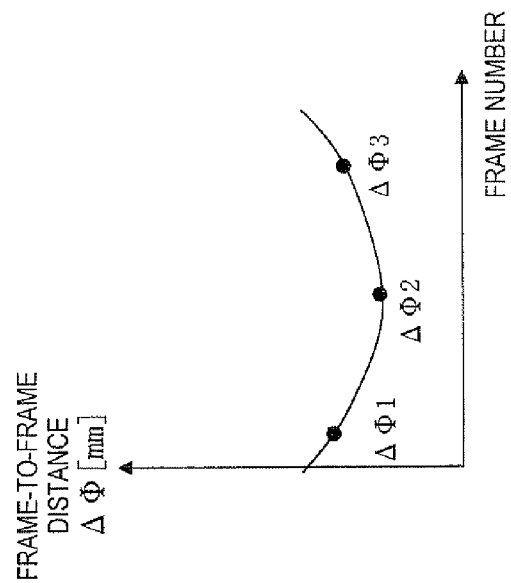
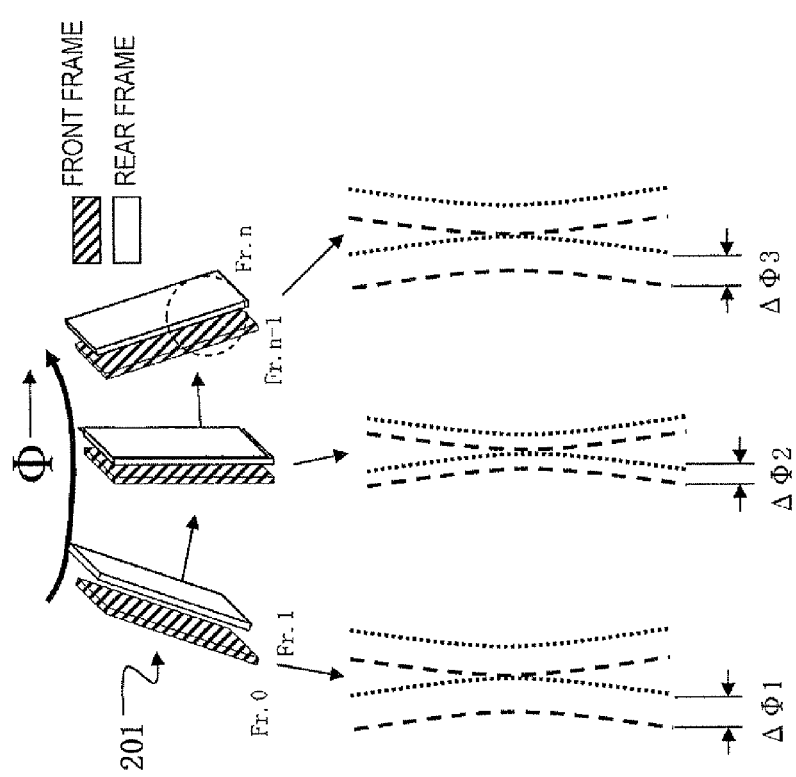

FIG. 7
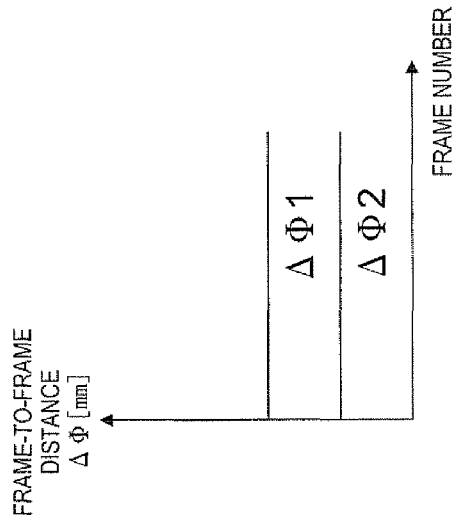
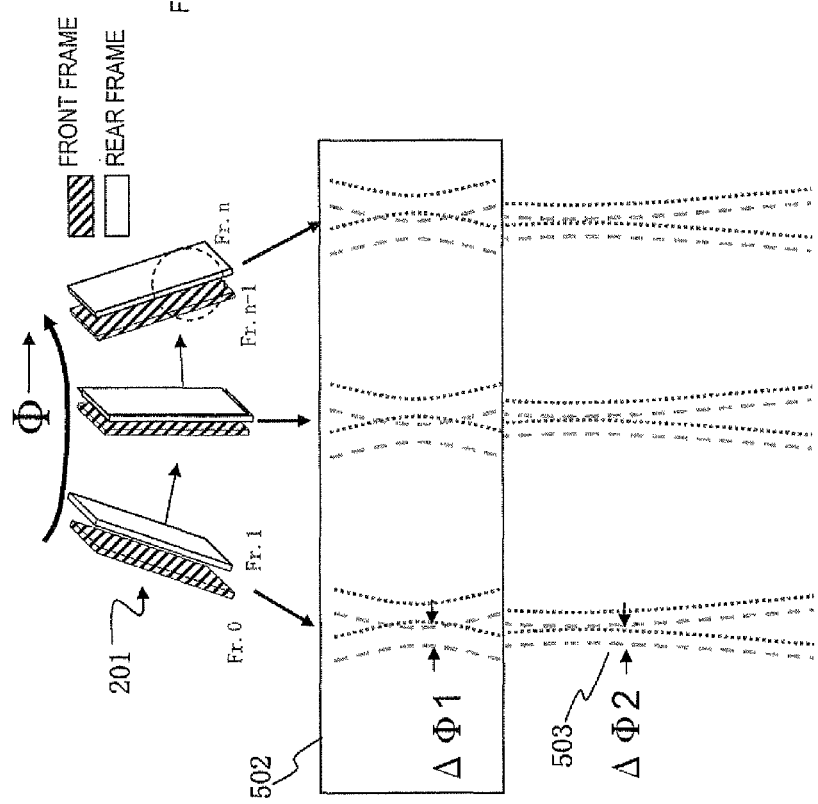

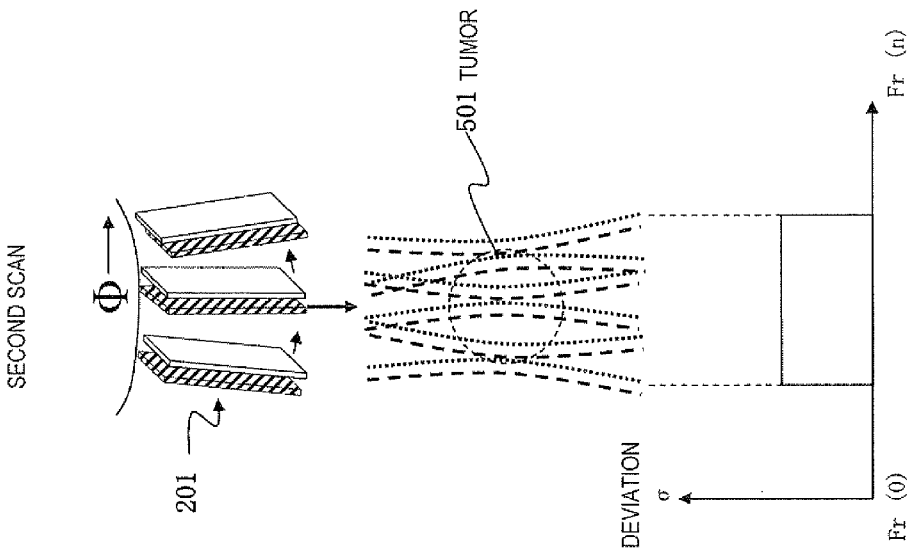
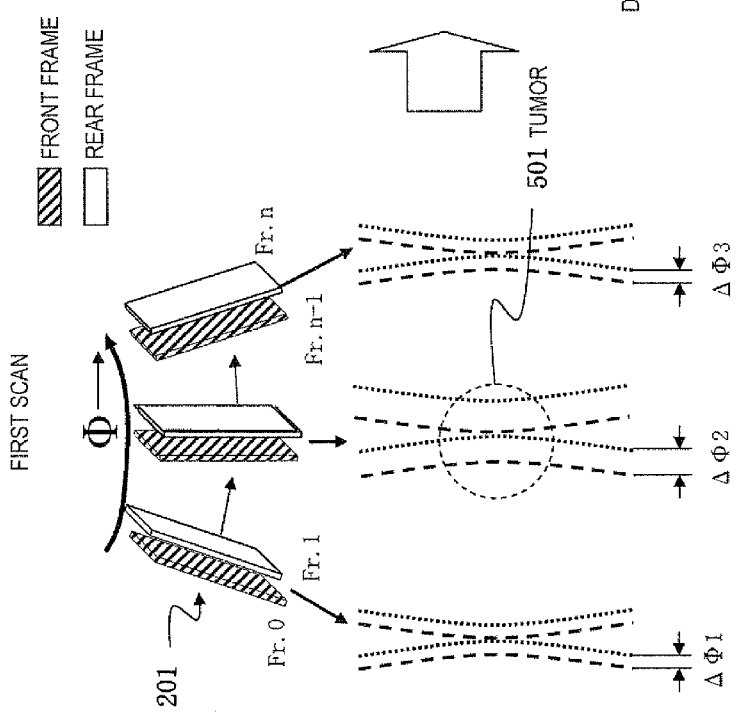
FIG. 11

FIG. 12
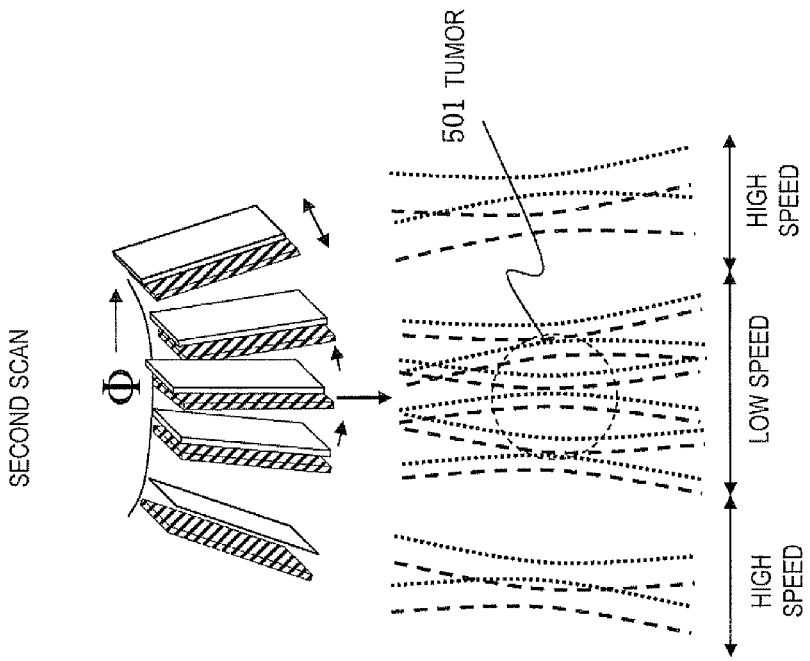
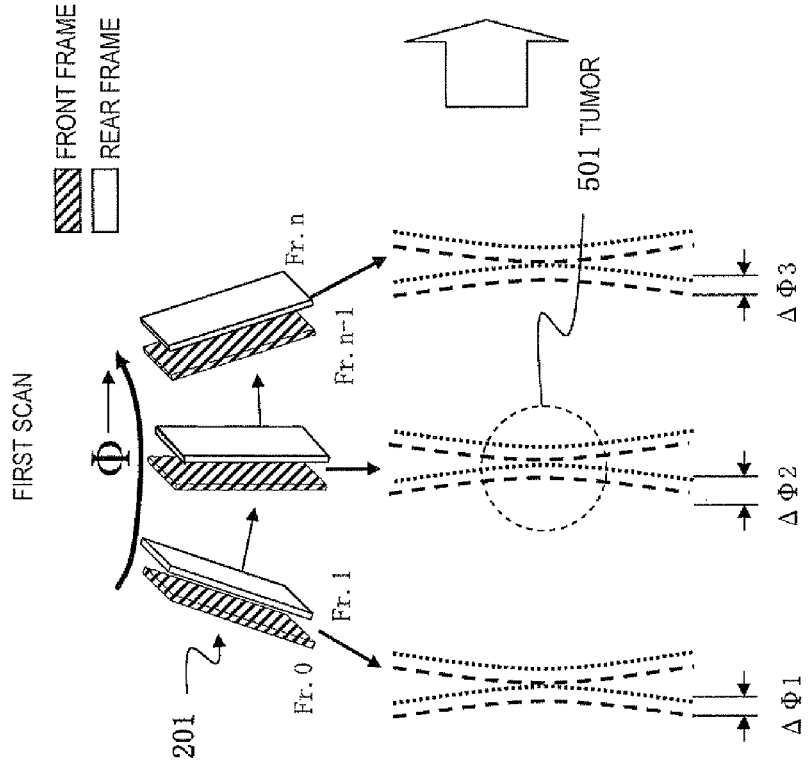

ULTRASONIC DIAGNOSTIC APPARATUS AND ELASTICITY IMAGE DISPLAY METHOD

TECHNICAL FIELD

The present invention relates to an ultrasonic diagnostic apparatus and an elasticity image display method and, more particularly, to elasticity image measurement suitable for shortening the time required to display an elasticity image indicating the hardness or softness of a living tissue in two or three dimensions.

BACKGROUND ART

An ultrasonic diagnostic apparatus performs ultrasonic scanning along an arbitrary cross-sectional plane inside an object by an ultrasonic probe and constructs and displays, for example, a tomographic image on the basis of RF signal frame data obtained by performing reception processing on a reflection echo signal from a living tissue at a cross-sectional position including the cross-sectional plane. Since RF signal frame data here is substantially identical to tomographic image data, the term tomographic image data in the description below conceptually includes RF signal frame data.

Also, it is commonly performed to repeatedly measure RF signal frame data at a single cross-sectional position while pressing an object with an ultrasonic probe, obtain displacements of parts of a living tissue at the cross-sectional position on the basis of two pieces of RF signal frame data different in measurement time (the amount of pressing), and construct an elasticity image indicating the hardness or softness of the living tissue on the basis of obtained displacement frame data (e.g., Patent Literature 1). Elasticity information indicating the hardness or softness of a living tissue is typically a strain or the elastic-modulus of the living tissue. It is, however, well-known that examples of elasticity information include a physical quantity, such as a displacement, correlating with a strain or an elastic-modulus.

Further, it is commonly performed to transmit/receive ultrasonic waves while moving an ultrasonic probe in a short axis direction orthogonal to a direction in which transducers are arranged (a long axis direction), measure respective two-dimensional tomographic images at different cross-sectional positions to generate volume data of the tomographic images, perform volume rendering using the volume data to construct a three-dimensional tomographic image (e.g., a two-dimensional projection image), and display the three-dimensional tomographic image (e.g., Patent Literature 2). In this case, a position sensor which measures the position and tilt of the ultrasonic probe is provided, position information and tilt information are acquired at the same time as transmission/reception of ultrasonic waves, and a plurality of two-dimensional tomographic images are registered in association with three-dimensional coordinates of volume data. With a three-dimensional tomographic image constructed in the above-described manner, information on the extent of a part of interest can be observed from a different angle.

Similarly, the process of constructing and displaying a three-dimensional elasticity image has been proposed in order to intuitively recognize the shape and volume of a hard part or a soft part present in a living tissue (e.g., Patent Literature 3). According to the process, elasticity image volume data composed of a plurality of two-dimensional elasticity images measured by general elasticity image measurement is generated, and a three-dimensional image (e.g., a two-dimensional projection image) is constructed on the basis of the elasticity image volume data. A further improvement in visibility by displaying a three-dimensional elasticity image to be superimposed on, e.g., a three-dimensional tomographic image has also been proposed.

CITATION LIST

Patent Literature

Patent Literature 1; JP-A-2000-060853
Patent Literature 2: JP-A-2006-271523
Patent Literature 3: JP-A-2008-259605

SUMMARY OF INVENTION

Technical Problem

Elasticity image volume data in Patent Literature 3 is generated by repeatedly measuring RF signal frame data at a single cross-sectional position while pressing an object, by elasticity image measurement disclosed in Patent Literature 1, obtaining a displacement of a living tissue at the single cross-sectional position on the basis of two pieces of RF signal frame data different in measurement time (the amount of pressing), constructing a two-dimensional elasticity image on the basis of obtained displacement frame data, and constructing respective two-dimensional elasticity images at a plurality of cross-sectional positions while moving an ultrasonic probe in a short axis direction.

That is, according to a conventional technique, elasticity image volume data is generated by obtaining a displacement of a living tissue between two pieces of RF signal frame data measured at a single cross-sectional position under different amounts of pressing, constructing one elasticity image from obtained displacement frame data, and constructing a plurality of elasticity images in the same manner while moving a current cross-sectional position in a short axis direction of an ultrasonic probe.

However, the need to construct an elasticity image by repeatedly measuring at least two pieces of RF signal frame data under different amounts of pressing at each of different cross-sectional positions causes the problem of the long measurement time for generating elasticity image volume data. Also, at least two pieces of RF signal frame data need to be stored for each cross-sectional position, which causes the problem of the increase in the size of memory for RF signal frame data.

Additionally, the operation of measuring two pieces of RF signal frame data under different amounts of pressing while manually changing the amount of pressing at a single cross-sectional position needs to be repeatedly performed while an ultrasonic probe is moved from one to another of a plurality of cross-sectional positions. The magnitudes of the amounts of pressing for two pieces of RF signal frame data and the difference between the amounts of pressing are preferably common among all cross-sectional positions. However, the process of manually operating an ultrasonic probe such that a plurality of cross-sectional positions are equal in the magnitudes of the amounts of pressing and the difference between the amounts of pressing is extremely difficult in practice, which is a problem.

For example, if cross-sectional positions are different in the magnitudes of the amounts of pressing and the difference between the amounts of pressing, pieces of displacement frame data in which displacements of a single living tissue at the cross-sectional positions have various values are measured. If elasticity images are constructed on the basis of the pieces of displacement frame data to generate volume data, and a three-dimensional elasticity image is constructed by volume rendering, pieces of elasticity information of the single living tissue on the three-dimensional elasticity image vary widely, and a sharp three-dimensional elasticity image may not obtained.

The present invention has as an object to implement elasticity image measurement which can shorten the time required to measure elasticity images and in which the degree of uniformity in the magnitudes of the amounts of pressing and the difference between the amounts of pressing at the time of elasticity image measurement is allowable. The present invention has as an object to shorten the time required to measure elasticity image volume data, in addition to the object.

Solution to Problem

In order to achieve the above objects, a first aspect of an ultrasonic diagnostic apparatus according to the present invention includes: an ultrasonic probe which transmits/receives ultrasonic waves to/from an object while being in contact with the object; a transmission/reception unit which, in a process in which pressing force applied to the object by the ultrasonic probe is changed and a cross-sectional position for transmitting/receiving ultrasonic waves to/from the object is moved in a short axis direction, periodically transmits/receives ultrasonic waves to/from the object, performs reception processing on a reflection echo signal from the object, and measures RF signal frame data at the cross-sectional position; a displacement measurement unit which, on the basis of two pieces of RF signal frame data, between which a difference in measurement time falls within a set range, selected from among a plurality of pieces of RF signal frame data sequentially measured by the transmission/reception unit, obtains a displacement of a living tissue at the cross-sectional position and sequentially generates displacement frame data; an elasticity information calculation unit which, on the basis of the displacement frame data sequentially generated by the displacement measurement unit, obtains elasticity information of the living tissue at the cross-sectional position and sequentially generates elasticity frame data; and an elasticity image construction unit which, on the basis of the elasticity frame data sequentially generated by the elasticity information calculation unit, sequentially constructs elasticity images.

That is, in a process in which the pressing force applied to the object by the ultrasonic probe being in contact with the object is changed and the cross-sectional position for transmitting/receiving ultrasonic waves is moved in the short axis direction, pieces of RF signal frame data at a plurality of consecutive cross-sectional positions are sequentially measured, a displacement of the living tissue at each of the cross-sectional positions is obtained on the basis of two of the pieces of RF signal frame data, between which a difference in measurement time falls within the set range, elasticity information of the living tissue at each cross-sectional position is obtained on the basis of displacement frame data, and elasticity images are sequentially constructed.

In other words, according to a conventional technique, a two-dimensional elasticity image is constructed by measuring two pieces of RF signal frame data under different amounts of pressing at each cross-sectional position and obtaining a displacement of a living tissue at the cross-sectional position (scan plane). A plurality of two-dimensional elasticity images are acquired while a current scan plane is sequentially shifted in a short axis direction, and elasticity image volume data for a region corresponding to a desired volume of an object is constructed. In contrast, a feature of the present invention lies in measuring two pieces of RF signal frame data under different amounts of pressing measured at different cross-sectional positions and obtaining a displacement of a living tissue at either one of the cross-sectional positions or at an average position of the two cross-sectional positions. As a result, according to the present invention, the number of RF signal frame data measurements can be reduced by at least one-half. This makes it possible to reduce the time required to measure elasticity image volume data by at least one-half. Also, a latest measured one of two pieces of RF signal frame data need not be stored in a memory, which allows a reduction in the size of the memory.

Note that, according to the present invention, two pieces of RF signal frame data, between which a displacement of a living tissue is to be obtained, are measured at different cross-sectional positions, which makes the accuracy of living tissue displacement data lower than that of a conventional technique. However, since RF signal frame data is periodically measured, changes in the amount of pressing and cross-sectional position between pieces of RF signal frame data are continuous. Additionally, since the period of measurement of RF signal frame data is much shorter than the time for a cross-sectional position to change, a plurality of pieces of displacement frame data, for which the degree of uniformity in the magnitudes of the amounts of pressing and the difference between the amounts of pressing is allowable, can be measured. As a result, a plurality of elasticity images, for which the degree of uniformity in the magnitudes of the amounts of pressing and the difference between the amounts of pressing is allowable, can be constructed.

Especially since two pieces of RF signal frame data, for which displacement frame data is to be obtained, are selected from among pieces of RF signal frame data, between which a difference in measurement time falls within the set range, a positional shift of the living tissue caused by a difference in cross-sectional position can be reduced to be negligibly small. For example, cross-sectional positions in a short axis direction of an ultrasonic probe are generally at intervals of, e.g., 0.05 to 0.1 mm, although the interval depends on the frame rate. Pieces of RF signal frame data are measured by swinging or linearly moving the ultrasonic probe. On the other hand, an ultrasonic beam diameter is about 1 mm. Accordingly, adjoining or adjacent cross-sectional positions mostly overlap with each other in living tissue, and a positional shift of the living tissue included in measured pieces of RF signal frame data is almost negligible in spite of the difference in cross-sectional position. In light of this, the set range for a difference in measurement time is preferably set such that diameters of ultrasonic reception beams of reflection echo signals at a plurality of the adjoining or adjacent cross-sectional positions overlap with each other. If measurement is performed while the ultrasonic probe is swung on a circular arc with a radius of, e.g., 80 mm, the interval between adjoining pieces of RF signal frame data to be measured widens according to depth. It is thus preferable to correct the interval in displacement calculation. However, even without correction, an error is negligibly small.

Note that a positional difference between two pieces of RF signal frame data at adjoining or adjacent cross-sectional positions is small and that the amount of pressing preferably changes at a constant rate of change between the two pieces of RF signal frame data. However, the rate of change in the amount of pressing between frames may not actually be constant. This case can be dealt with normalization of an elasticity image with an average value of elasticity information (e.g., a strain). Pressing force may be mechanically applied. Since manually applied pressing force can be appropriately adjusted, manual application is advantageous in ease of measurement and ease of use for, e.g., mass screening.

Also, a second aspect of the ultrasonic diagnostic apparatus according to the present invention includes, in addition to the first aspect, a volume data generating unit which sequentially registers the elastic images constructed by the elasticity image construction unit in a memory together with respective pieces of positional information of the cross-sectional position and a three-dimensional elasticity image construction unit which constructs a three-dimensional elasticity image by rendering on the basis of volume data of the elasticity images registered in the volume data generating unit and displays the three-dimensional elasticity image on a monitor screen.

According to the second aspect, in addition to the capability to reduce the time required to measure volume data of elasticity images by at least one-half, a three-dimensional elasticity image can be constructed and displayed. Accordingly, the shape and volume of a hard part or a soft part present in a living tissue can be intuitively recognized. Also, visibility can be further improved by displaying a three-dimensional elasticity image to be superimposed on, e.g., a three-dimensional tomographic image.

The first aspect of the present invention can further include a swing device including a swing mechanism which swings the ultrasonic probe in the short axis direction, a motor which swings and drives the ultrasonic probe via the swing mechanism, and a motor control unit which senses a swing angle of the ultrasonic probe from a rotational position of the motor and controls a rotational speed of the motor. In this case, the first aspect includes a volume data generating unit which sequentially registers the elastic images constructed by the elasticity image construction unit in a memory in association with respective swing angles of the ultrasonic probe and a three-dimensional elasticity image construction unit which constructs a three-dimensional elasticity image by rendering on the basis of volume data of the elasticity images registered in the volume data generating unit and displays the three-dimensional elasticity image on a monitor screen.

According to this configuration, the ultrasonic probe is swung by the motor, and swing operation can be stabilized. Since a tester only needs to watch for a change in the amount of pressing, the tester can easily generate elasticity image volume data. Also, the present invention can be implemented only by making a simple change to a general ultrasonic diagnostic apparatus capable of measuring an elasticity image.

If three or more pieces of RF signal frame data are measured within the set range for the difference in measurement time, the displacement measurement unit can obtain a correlation of a latest one of the pieces of RF signal frame data with each of the other pieces of RF signal frame data measured within the set range and obtain the displacement frame data between the two pieces of RF signal frame data with a highest correlation.

In the first or second aspect of the present invention, the transmission/reception unit can be adapted to transmit preset ultrasonic waves for elasticity image acquisition and preset ultrasonic waves for tomographic image acquisition as a set to a plurality of the consecutive cross-sectional positions and the one subsequent cross-sectional position, respectively, a period of transmission of ultrasonic waves for elasticity image acquisition being set to a period that causes diameters of ultrasonic reception beams of sequentially received reflection echo signals to overlap with each other. In this case, the first aspect or second aspect can further include a tomographic image construction unit which constructs a tomographic image on the basis of RF signal frame data measured by the transmission/reception unit in response to the ultrasonic waves for tomographic image acquisition. According to this configuration, patterns (e.g., frequency, pulse pattern, and intensity) of ultrasonic waves suitable for elasticity image acquisition and for tomographic image acquisition can be used. The image quality of an elasticity image, that of a tomographic image, and the like can be improved.

The motor control unit can control speed of the motor in a pattern with a swing speed decreasing from a center of a swing range of the ultrasonic probe toward two ends. According to this configuration, a distance between adjoining frames is larger at the two ends of the swing range, and a deviation of an angle of an ultrasonic beam with respect to a pressing direction increases, which reduces the resolution of an elasticity image. However, a lower swing speed allows an increase in resolution.

The motor control unit can control the swing speed of the ultrasonic probe according to a depth for one of a plurality of depth sections into which a range in a depth direction is divided, and the elasticity image construction unit can construct an elasticity image on the basis of the RF signal frame data measured for each depth section.

The motor control unit can control the swing speed of the ultrasonic probe according to depth of a part of interest desired to be observed in the three-dimensional elasticity image. With this configuration, since a distance between frames is small when the depth of the part of interest is shallow, resolution is maintained by increasing the swing speed. Conversely, since a distance between frames is larger and the resolution is lower when the depth is deep, the resolution is maintained by reducing the swing speed.

The motor control unit can periodically control the swing speed of the ultrasonic probe to increase and decrease, and the elasticity image construction unit can construct the elasticity image on the basis of the RF signal frame data measured in a swing section where the swing speed is low. That is, thinning of elasticity images to be constructed allows a reduction in rendering load and speedup. Also, an increase in the density of elasticity images in the section where the swing speed is low makes it possible to inhibit the image quality of an elasticity image from being degraded due to the thinning.

The elasticity volume data generating unit can merge a plurality of elasticity images sequentially constructed by the elasticity image construction unit into one elasticity image and sequentially register the elasticity image after the merging in the memory in association with an average swing angle of a plurality of cross-sectional positions corresponding to the plurality of elasticity images. According to this configuration, since a plurality of two-dimensional elasticity images can be converted into one two-dimensional elasticity image, i.e., can be averaged, artifacts can be reduced, and volume data can be reduced, which allows speedup of rendering.

The motor control unit can periodically control the swing speed of the ultrasonic probe to increase and decrease, the elasticity image construction unit can construct the elasticity image on the basis of the RF signal frame data measured in a swing section where the swing speed is low, and the volume data generating unit can merge a plurality of elasticity images sequentially constructed by the elasticity image construction unit into one elasticity image and sequentially register the elasticity image after the merging in the memory in association with an average swing angle of a plurality of cross-sectional positions corresponding to the plurality of elasticity images. According to this configuration, since elasticity images to be constructed are thinned out, the image quality of an elasticity image is inhibited from being degraded by increasing the density of elasticity images in the section where the swing speed is low. Also, thinning of elasticity images to constitute volume data allows a reduction in rendering load and speedup.

Also, the motor control unit can control the swing speed of the ultrasonic probe to be low in a specific swing section corresponding to a plurality of cross-sectional positions including the part of interest desired to be observed in the three-dimensional elasticity image and control the swing speed to be high outside the specific swing section. According to this configuration, rendering processing can be speeded up by reducing the swing speed in a frame acquisition section for rendering and increasing the swing speed in other sections.

The motor control unit can perform control according to the variably set swing speed of the ultrasonic probe in the specific swing section corresponding to the plurality of cross-sectional positions including the part of interest desired to be observed in the three-dimensional elasticity image.

Additionally, the motor control unit can control the swing speed to be low in the specific swing section corresponding to the plurality of cross-sectional positions including the part of interest desired to be observed in the three-dimensional elasticity image, and the volume data generating unit can convert the plurality of elasticity images sequentially constructed by the elasticity image construction unit into one elasticity image and sequentially register the elasticity image in a memory in association with an average swing angle of a plurality of cross-sectional positions corresponding to the plurality of elasticity images.

The elasticity information calculation unit can include a part-of-interest detection unit which detects on the basis of the elasticity frame data and in light of a preset condition whether a part of interest desired to be observed in the three-dimensional elasticity image is included, and the motor control unit can control swing speed of the ultrasonic probe to be low in response to a signal indicating detection of the part of interest output from the part-of-interest detection unit and control the swing speed of the ultrasonic probe to be high when the signal indicating detection of the part of interest is not output from the part-of-interest detection unit. Alternatively, an input setting unit which inputs and sets a part of interest desired to be observed in the three-dimensional elasticity image can be included, the motor control unit can control the swing speed of the ultrasonic probe to be low in the part of interest input from the input setting unit and control the swing speed of the ultrasonic probe to be high outside the part of interest. According to these configurations, it is possible to detect or set a section where a part of interest is to be imaged, reduce the swing speed in a part of interest, and increase the swing speed outside the part of interest. This allows an increase in immediacy.

A tomographic image construction unit which constructs a tomographic image on the basis of the RF signal frame data is further included, the transmission/reception unit performs transmission/reception of ultrasonic waves for measuring the RF signal frame data at a plurality of the cross-sectional positions a plurality of times, the tomographic image construction unit includes a part-of-interest detection unit which detects a part of interest meeting a preset condition as a part to be observed in the three-dimensional elasticity image on the basis of the tomographic image obtained by initial measurement of the RF signal frame data, the motor control unit switches swing speed of the ultrasonic probe at a plurality of cross-sectional positions including the part of interest to a low speed at the time of measurement of the RF signal frame data after the part-of-interest detection unit detects the part of interest, and the elasticity image construction unit can construct the elasticity images on the basis of the RF signal frame data measured at the plurality of cross-sectional positions including the part of interest within a swing range of the ultrasonic probe. According to this configuration, the time required to generate elasticity image volume data can be shortened, the size of memory for volume data can be reduced, and a high-definition three-dimensional elasticity image can be constructed.

An elasticity image display method according to the present invention can include: a first step of, in a process in which pressing force applied to an object by an ultrasonic probe is changed and a cross-sectional position for transmission/reception of ultrasonic waves is moved in a short axis direction, periodically transmitting/receiving ultrasonic waves to/from the object and capturing a measured reflection echo signal by the ultrasonic probe; a second step of performing reception processing on the reflection echo signal captured in the first step and periodically measuring RF signal frame data; a third step of, on the basis of two pieces of RF signal frame data, between which a difference in measurement time falls within a set range, selected from among a plurality of pieces of RF signal frame data periodically measured in the second step, obtaining displacements of a living tissue at a plurality of the cross-sectional positions and sequentially generating pieces of displacement frame data; a fourth step of, on the basis of a plurality of the pieces of the displacement frame data obtained in the third step, calculating elasticity information of the living tissue at the plurality of cross-sectional positions and sequentially generating elasticity frame data; and a fifth step of, on the basis of the elasticity frame data sequentially generated in the fourth step, sequentially constructing elasticity images.

In this case, the method can include: a sixth step of sequentially registering the elasticity images sequentially generated in the fifth step in a memory together with respective pieces of positional information of the corresponding cross-sectional positions to generate volume data of the elasticity images; and a seventh step of constructing a three-dimensional elasticity image by rendering using the volume data generated in the sixth step and displaying the three-dimensional elasticity image on a monitor screen.

In this case, the first step is performed by a swing device including a swing mechanism which swings the ultrasonic probe in the short axis direction, a motor which swings and drives the ultrasonic probe via the swing mechanism, and a motor control unit which senses a swing angle of the ultrasonic probe from a rotational position of the motor and controls a rotational speed of the motor, the sixth step can include sequentially registering the constructed elasticity images in the memory in association with respective swing angles of the ultrasonic probe to generate volume data, and the seventh step can include constructing a three-dimensional elasticity image by rendering on the basis of the volume data of the registered elasticity images and displaying the three-dimensional elasticity image on the monitor screen.

Further, in this case, the method includes a ninth step of constructing a tomographic image on the basis of the RF signal frame data. In the first step, transmission/reception of ultrasonic waves for measuring the RF signal frame data at a plurality of the cross-sectional positions is performed a plurality of times. The fifth step includes an eighth step of, on the basis of the tomographic image obtained by initial measurement of the RF signal frame data, detecting a part of interest meeting a preset condition as a part to be observed in the three-dimensional elasticity image. The motor control unit can switch swing speed of the ultrasonic probe at a plurality of cross-sectional positions including the part of interest to a low speed at the time of measurement of the RF signal frame data in the first step after the part of interest is detected in the eighth step and construct the elasticity image on the basis of the RF signal frame data measured at the plurality of cross-sectional positions including the part of interest within a swing range of the ultrasonic probe in the fifth step.

Advantageous Effect of Invention

According to the present invention, elasticity image measurement which can shorten the time required to measure elasticity images and in which the degree of uniformity in the magnitudes of the amounts of pressing and the difference between the amounts of pressing at the time of elasticity image measurement is allowable can be implemented. This makes it possible to shorten the time required to measure elasticity image volume data.

BRIEF DESCRIPTION OF DRAWINGS

FIG. 3 are views for explaining elasticity image measurement according to a first embodiment of the present invention.

FIG. 4 are views for explaining a method for mechanically swinging an ultrasonic probe in a short axis direction while manually changing the degree of pressing using a swing device for an ultrasonic probe to measure a plurality of elasticity images and displaying a three-dimensional elasticity image by a rendering method using volume data composed of the plurality of elasticity images.

FIG. 5 are views for explaining elasticity image measurement according to a second embodiment of the present invention.

FIG. 6 are figures for explaining elasticity image measurement according to a third embodiment of the present invention.

FIG. 7 are figures for explaining elasticity image measurement according to a fourth embodiment of the present invention.

FIG. 11 are figures for explaining elasticity image measurement according to an eighth embodiment of the present invention.

FIG. 12 are views for explaining elasticity image measurement according to a ninth embodiment of the present invention.

DESCRIPTION OF EMBODIMENTS

Figure 1:
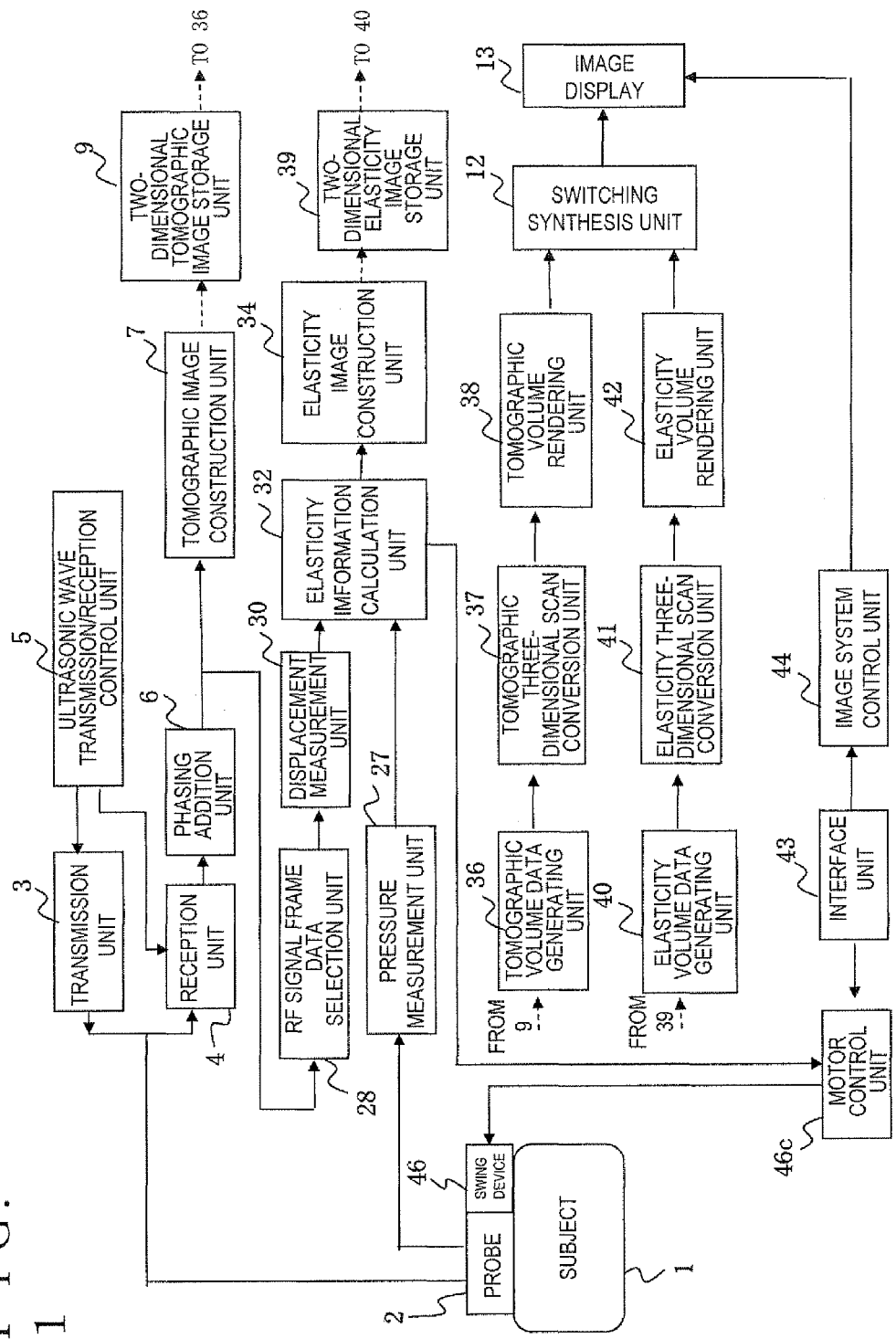
FIG. 1 is a block configuration diagram of an embodiment of an ultrasonic diagnostic apparatus to which a method for acquiring an elasticity image according to the present invention.

FIG. 1 is a block configuration diagram of an embodiment of an ultrasonic diagnostic apparatus to which elasticity image measurement according to the present invention is applied. As shown in FIG. 1, the ultrasonic diagnostic apparatus includes an ultrasonic probe 2 which is used in contact with an object 1, a transmission unit 3 which periodically and repeatedly transmits ultrasonic waves to the object 1 via the ultrasonic probe 2 at time intervals, a reception unit 4 which receives time-series reflection echo signals originating in the object 1, a transmission/reception control unit 5 which performs control to switch between transmission by the transmission unit 3 and reception by the reception unit 4, and a phasing addition unit 6 which phases and adds reflection echo signals received by the reception unit 4. The transmission unit 3, reception unit 4, transmission/reception control unit 5, and phasing addition unit 6 constitute a transmission/reception unit.

The ultrasonic probe 2 is formed such that a plurality of transducers are arranged in a straight line or in convex form and has the function of transmitting/receiving ultrasonic waves to a cross-sectional position of the object 1 via the transducers. The ultrasonic probe 2 is assembled to a swing device 46 provided with, for example, a swing mechanism of the guide rail type shown in FIG. 2(a) or the gear swing type shown in FIG. 2(b) and is configured as a mechanical 3D probe. However, the mechanical 3D probe is not limited to the types. In short, the mechanical 3D probe may be of any type as long as the mechanical 3D probe includes the swing device 46 capable of swinging an ultrasonic wave transmission/reception surface of the ultrasonic probe 2 in a short axis direction, i.e., in a direction orthogonal to a long axis direction in which the plurality of transducers are arranged.

For example, the swing device 46 provided with a swing mechanism of the guide rail type includes an arcuate guide rail 46a which guides the ultrasonic probe 2 so as to swing in the short axis direction, a motor 46b which drives to swing the ultrasonic probe 2 along the guide rail 46a, and a motor control unit 46c which senses a swing angle φ of the ultrasonic probe 2 with respect to the position shown in FIG. 2(a) on the basis of the rotation angle position of the motor 46b and controls the rotational speed of the motor 46b. In contrast, the swing device 46 provided with a swing mechanism of the gear swing type includes a gear 46d which supports a holding portion of the ultrasonic probe 2 so as to be swingable, the motor 46b that rotates a gear 46e engaging with the gear 46d, and the motor control unit 46c that senses a swing of the ultrasonic probe 2 on the basis of the rotation angle position of the motor 46b and controls the rotational speed of the motor 46b. With the above-described configuration, the motor control unit 46c drives to control the rotation angle of the motor 46b. This allows the ultrasonic probe 2 to swing along the guide rail 46a or about an axis of the gear 46d.

The motor control unit 46c is also adapted to detect a swing sensed by the ultrasonic probe 2 as a frame number on the basis of the rotational position of the motor 46b and the like at the same time as transmission/reception of ultrasonic waves by the transmission/reception unit.

The ultrasonic probe 2 is adapted to scan and transmit an ultrasonic beam to a cross-sectional position (scan plane) and receive a reflection echo signal from the object 1 by the transmission/reception unit while being mechanically swung by the motor 46b in the direction (short axis direction) orthogonal to the direction (long axis direction), in which the plurality of transducers are arranged. Note that the ultrasonic probe 2 is not limited to this. The ultrasonic probe 2 can be formed such that a plurality of transducers are arranged in two dimensions and can be adapted to have the function of electronically scanning the plurality of transducers in the short axis direction of the ultrasonic probe 2 by the transmission/ reception unit. In this case, movement in the short axis direction at a cross-sectional position can be implemented by a swing at the time of electronic scanning by the transmission/reception unit.

The transmission unit 3 generates a wave transmission pulse for driving the transducers of the ultrasonic probe 2 and causing the transducers to generate ultrasonic waves. The transmission unit 3 has the function of setting a convergent point of transmitted ultrasonic waves to some depth. The reception unit 4 amplifies a reflection echo signal received by the ultrasonic probe 2 with a predetermined gain and generates an RF signal, i.e., a reception signal. The transmission/reception control unit 5 is intended to control the transmission unit 3 and the reception unit 4. The phasing addition unit 6 receives an RF signal amplified by the reception unit 4 and subjects the RF signal to phase control. The phasing addition unit 6 forms an ultrasonic reception beam for one or more convergent points, and generates RF signal frame data that is tomographic image data.

A tomographic image construction unit 7 receives RF signal frame data output from the phasing addition unit 6, subjects the RF signal frame data to signal processing such as gain correction, log compression, wave detection, edge enhancement, and filter processing, and constructs a tomographic image. Note that although not shown, the ultrasonic diagnostic apparatus includes a monochrome scan converter which performs coordinate system conversion on a tomographic image synchronous with ultrasonic scanning output from the tomographic image construction unit 7 to obtain coordinates displayable by the scanning system of an image display 13. A tomographic image output from the monochrome scan converter is stored in a two-dimensional tomographic image storage unit 9 together with a frame number.

A tomographic volume data generating unit 36 reads out tomographic images for n frames stored in the two-dimensional tomographic image storage unit 9, arranges the tomographic images in the order of cross-sectional positions (scan planes), and creates tomographic volume data. In the above-described manner, tomographic volume data for rendering that is a collection of tomographic images of the interior of an object is generated.

A tomographic volume rendering unit 38 reads out tomographic volume data from the tomographic volume data generating unit 36 and constructs, as a monochrome three-dimensional tomographic image, a two-dimensional projection tomographic image obtained by projecting the tomographic volume data onto, e.g., a plane. More specifically, the tomographic volume rendering unit 38 obtains image information of each of points (coordinates) of the tomographic volume data from a brightness value and opacity corresponding to the point. The tomographic volume rendering unit 38 constructs the three-dimensional tomographic image by a volume rendering method that calculates a brightness value and opacity in a depth direction from a brightness value and opacity of the tomographic volume data in a view direction to produce light and shade according to, for example, the expression below.

$$\alpha out_i = \alpha in_i + (1 - \alpha in_i) * \alpha_i,$$

$$C out_i = C in_i + (1 - \alpha in_i) * \alpha_i * C_i \quad \text{(Expression 1)}$$

where
  $\alpha out_i$ is the i-th output opacity,
  $\alpha in_i$ is the i-th input opacity,
  $\alpha_i$ is the i-th opacity,
  $C out_i$ is the i-th output brightness value,
  $C in_i$ is the i-th input brightness value, and
  $C_i$ is the i-th brightness value.

Note that although a three-dimensional tomographic image is constructed using the volume rendering method in the above description, a surface rendering method that produces light and shade according to a tilt angle which an image at each point forms with a plane corresponding to an eye position or a voxel method that produces light and shade according to the depth of an object as seen from an eye position may be used.

A switching synthesis unit 12 is adapted to display a three-dimensional tomographic image constructed by the tomographic volume rendering unit 38 on the image display 13. The switching synthesis unit 12 is also adapted to merge the three-dimensional tomographic image with a color three-dimensional elasticity image (to be described later), display images in parallel, and switch between the two. Accordingly, the image display 13 is adapted such that a three-dimensional tomographic image, a color three-dimensional elasticity image, and a composite image of the three-dimensional tomographic image and the color three-dimensional elasticity image are displayed.

On the other hand, RF signal frame data periodically output from the phasing addition unit 6 is input to an RF signal frame data selection unit 28, and pieces of RF signal frame data are sequentially stored. The RF signal frame data selection unit 28 is adapted to select a stored piece of RF signal frame data and an input latest piece of RF signal frame data as one pair. The two pieces of RF signal frame data selected by the RF signal frame data selection unit 28 are two pieces of RF signal frame data, between which a difference in measurement time falls within a set range, of a plurality of periodically measured pieces of RF signal frame data. The set range for a difference in measurement time between two pieces of RF signal frame data to be selected can be set to a difference in measurement time that causes the diameters of ultrasonic reception beams of reflection echo signals at a plurality of cross-sectional positions (scan planes) to overlap with each other. Alternatively, the set range for a difference in measurement time between two pieces of RF signal frame data to be selected can be set to a difference in measurement time that causes the diameters of ultrasonic reception beams of reflection echo signals at adjoining cross-sectional positions to overlap with each other.

A displacement measurement unit 30 obtains a displacement of a living tissue at a scan plane on the basis of two pieces of RF signal frame data selected by the RF signal frame data selection unit 28, sequentially generates pieces of displacement frame data, and outputs the pieces of displacement frame data to an elasticity information calculation unit 32. That is, the displacement measurement unit 30 performs one-dimensional or two-dimensional correlation processing and obtains displacement frame data that is a one-dimensional or two-dimensional displacement distribution regarding a displacement and a motion vector (i.e., the direction and magnitude of the displacement) in a living tissue corresponding to each point (e.g., a pixel) on an image of the RF signal frame data from a selected piece of RF signal frame data with a frame number of "N." For example, a block matching method is used to detect a motion vector. The block matching method includes dividing an image into blocks of, e.g., M×M pixels, focusing on a block in a region of interest, searching for a block most similar to the block of interest in a previous frame, and performing prediction coding, i.e., the process of determining a sample value on the basis of a difference while referring to the block.

The elasticity information calculation unit 32 is adapted to obtain elasticity information such as a displacement or the elastic-modulus of a living tissue at a scan plane on the basis of each of sequentially input pieces of displacement frame data to sequentially generate pieces of elasticity frame data and output the pieces of elasticity frame data to an elasticity image construction unit 34. More specifically, the elasticity information calculation unit 32 calculates a strain of a living tissue at each pixel (coordinates) on an image as a piece of elasticity information on the basis of each piece of displacement frame data (e.g., motion vector data of a pixel) output from the displacement measurement unit 30. At this time, the strain is calculated by spatial differentiation of movement (e.g., a displacement) of the living tissue.

If the elasticity information calculation unit 32 calculates an elastic-modulus, a pressure applied to a living tissue of each part of a scan plane measured by a pressure measurement unit 27 which is connected to a pressure sensor (not shown) of the ultrasonic probe 2 is output to the elasticity information calculation unit 32. An elastic-modulus is calculated by dividing a change in pressure by a change in strain. For example, let L(X) be a displacement of each part of a living tissue measured by the displacement measurement unit 30. Since a strain ΔS(X) at the point can be calculated by spatial differentiation of L(X), the strain ΔS(X) can be obtained using the equation ΔS(X)=ΔL(X)/ΔX.

Letting P(X) be a pressure measured by the pressure measurement unit 27, a Young's modulus Ym(X) of elasticity can be calculated by the equation Ym=(ΔP(X))/ΔS(X). Since the elastic-modulus of a living tissue corresponding to each point can be obtained from the Young's modulus Ym, two-dimensional elasticity images can be consecutively obtained. Note that Young's modulus is the ratio of a simple tensile stress applied to an object to a strain occurring parallel to the tension.

The elasticity image construction unit 34 sequentially constructs pieces of elasticity image data on the basis of sequentially input pieces of elasticity frame data. More specifically, the elasticity image construction unit 34 subjects each calculated piece of elasticity information (e.g., a strain or an elastic-modulus) to various image processes such as smoothing processing between frames in a coordinate plane, contrast optimization processing, and smoothing processing between frames in a direction of time axis and constructs two-dimensional elasticity image data. Note that although not shown, an elasticity scan converter which performs coordinate system conversion on two-dimensional elasticity image data synchronous with ultrasonic scanning output from the elasticity image construction unit 34 to obtain coordinates displayable by the scanning system of the image display 13 is provided. Two-dimensional elasticity image data output from the elasticity scan converter is stored in a two-dimensional elasticity image storage unit 39 together with a frame number of "N."

A plurality of pieces of two-dimensional elasticity image data stored in the two-dimensional elasticity image storage unit 39 are read out by an elasticity volume data generating unit 40. The elasticity volume data generating unit 40 creates elasticity volume data of the elasticity images. More specifically, the elasticity volume data generating unit 40 reads out pieces of two-dimensional elasticity image data with a series of frame numbers of "1" to "n" stored in the two-dimensional elasticity image storage unit 39, arranges the pieces of two-dimensional elasticity image data in the order of scan planes, and creates elasticity volume data. In the above-described manner, elasticity volume data for rendering that is a collection of pieces of two-dimensional elasticity image data of the interior of an object is constructed.

Elasticity volume data created by the elasticity volume data generating unit 40 is appropriately read out by an elasticity volume rendering unit 42, and a color three-dimensional elasticity image is constructed. The constructed color three-dimensional elasticity image is displayed on the image display 13 via the switching synthesis unit 12. More specifically, the elasticity volume rendering unit 42 obtains the image information of each point of an image of elasticity volume data from elasticity information (either one of a strain, an elastic-modulus, and the like) and opacity corresponding to the point and constructs a three-dimensional elasticity image. For example, the elasticity volume rendering unit 42 constructs a three-dimensional elasticity image by, e.g., the volume rendering method that calculates elasticity in a depth direction from elasticity of elasticity volume data in a view direction according to Expression 2 below. Note that the view direction is the same direction as the view direction in volume rendering processing by the tomographic volume rendering unit 38 and the like.

$$\alpha out i = \alpha in i + (1-\alpha in i)*\alpha i,$$

$$E out i = E in i + \alpha i *(1-\alpha in i)*E i \quad \text{(Expression 2)}$$

where
  $\alpha out i$ is the i-th output opacity,
  $\alpha in i$ is the i-th input opacity,
  $\alpha i$ is the i-th opacity,
  $E out i$ is the i-th output elasticity value,
  $E in i$ is the i-th input elasticity value, and
  $E i$ is the i-th elasticity value.

The elasticity volume rendering unit 42 also gives light's three primary colors, i.e., a red (R) value, a green (G) value, and a blue (B) value to each of pieces of image information constituting a three-dimensional elasticity image. For example, the elasticity volume rendering unit 42 gives a red code to a part with a larger strain than its surroundings or a part with a lower elastic-modulus, gives a blue code to a part with a smaller strain than its surroundings or a part with a higher elastic-modulus, and performs other processes.

The detailed configuration of the switching synthesis unit 12 will now be described. The switching synthesis unit 12 includes an image memory, an image processing unit, and an image selection unit. The image memory stores a monochrome three-dimensional tomographic image output from the tomographic volume rendering unit 38 and a color three-dimensional elasticity image output from the elasticity volume rendering unit 42 together with time information. The image processing unit changes the synthesis ratio of monochrome three-dimensional tomographic image data and color three-dimensional elasticity image data stored in the image memory and superimposes the pieces of image data in the changed synthesis ratio. The image processing unit reads out three-dimensional tomographic image data and color three-dimensional elasticity image data at the same eye position from the image memory.

Since three-dimensional tomographic image data and color three-dimensional tomographic image data are pieces of image data having undergone volume rendering processing and the like, the image processing unit substantially two-dimensionally adds the three-dimensional tomographic image data and color three-dimensional elasticity image data when merging the pieces of image data. More specifically, the image processing unit adds a red (R) value, a green (G) value, and a blue (B) value of a piece of color three-dimensional elasticity image data and a red (R) value, a green (G) value, and a blue (B) value, respectively, of a piece of three-dimensional tomographic image data at each point on an image, as given by, e.g., Expressions 3 below. Note that the symbol α is a coefficient not less than 0 and not more than 1 and is arbitrarily set by an interface unit 43.

(Expressions 3)

$$\text{(Composite Image Data } R) = \alpha \times \text{(Color Three-Dimensional Elasticity Image Data } R) + (1-\alpha) \times \text{(Three-Dimensional Tomographic Image Data } R)$$

$$\text{(Composite Image Data } G) = \alpha \times \text{(Color Three-Dimensional Elasticity Image Data } G) + (1-\alpha) \times \text{(Three-Dimensional Tomographic Image Data } G)$$

$$\text{(Composite Image Data } B) = \alpha \times \text{(Color Three-Dimensional Elasticity Image Data } B) + (1-\alpha) \times \text{(Three-Dimensional Tomographic Image Data } B)$$

For example, only three-dimensional tomographic image data or color three-dimensional elasticity image data can also be extracted by setting the coefficient α to 0 or 1. The image selection unit selects an image (images) to be displayed on the image display 13 from among three-dimensional tomographic image data and color three-dimensional elasticity image data in the volume memory and composite image data of the image processing unit. The image display 13 displays a composite image formed by the switching synthesis unit 12 and a three-dimensional tomographic image or a color three-dimensional elasticity image in parallel.

As described above, according to the present embodiment, a three-dimensional elasticity image indicating the hardness or softness of a living tissue of an object can be constructed and displayed.

The ultrasonic diagnostic apparatus also includes an image system control unit 44 which controls each component and the interface unit 43 that supplies various inputs to the image system control unit 44. The interface unit 43 includes a keyboard and a trackball.

The procedure for measuring two-dimensional elasticity images from which elasticity image volume data that is a feature of the present invention is constructed will be described below with reference to first to tenth embodiments. The each embodiment to be described below has in common the points below, and a corresponding description may be appropriately omitted. (1) Pressing of the object 1 is manually performed with the ultrasonic probe 2 in contact with the object 1.

However, the present invention is not limited to this. Mechanical pressing or pressing with a liquid balloon can be used instead. Also, pressing is performed to a degree that the object 1 is deformed by, e.g., up to about 20 mm. Further, it is preferable that the object 1 is deformed by up to about 20 mm during one swing period. (2) Ultrasonic waves are transmitted/received while the ultrasonic probe 2 of the mechanical 3D probe is swung along a curved surface (arcuate surface) set in the short axis direction. Tomographic images are consecutively acquired. The ultrasonic probe 2 may be swung to one side or may be swung from side to side within a predetermined angle range (e.g., 30°). Note that the ultrasonic probe 2 may be manually swung in the short axis direction without the mechanical 3D probe. Movement of the ultrasonic probe 2 in the short axis direction is not limited to a swing, and the ultrasonic probe 2 can be linearly moved while being slid on the surface of the body of the object 1. (3) The period of transmission/reception of ultrasonic waves from/to the ultrasonic probe 2 is fixed, and the period of measurement of RF signal frame data (the frame rate) is fixed.

First Embodiment

A processing procedure according to the first embodiment of elasticity image measurement will be described with reference to FIG. 3. FIG. 3(a) shows the process of measuring pieces 201 of tomographic image data with frame numbers of Fr.0 to Fr.n while mechanically swinging an ultrasonic probe 2 in a short axis direction using a mechanical 3D probe in FIG. 2 and moving a scan plane for transmitting/receiving ultrasonic waves in a direction of ϕ to sequentially change a swing angle (swinging the scan plane). FIG. 3(b) shows three-dimensional acquisition of two-dimensional tomographic image data, i.e., the process of three-dimensionally acquiring tomographic image data while regarding a direction of a plurality of frames of two-dimensional tomographic image data as one line. It is generally desirable to perform correlation calculation on a single scan plane, i.e., at a single frame position to calculate a displacement when constructing an elasticity image. However, detection of a displacement using adjoining or adjacent pieces of ultrasonic tomographic image data with different frame numbers is a feature of the present embodiment. For example, the interval between adjoining frames is represented by the symbol Δϕ using the letter ϕ denoting the swing angle of the ultrasonic probe 2.

In the present embodiment, the frame numbers of Fr.0 to Fr.n of pieces of tomographic image data obtained at the adjoining frame intervals Δϕ associate swing angles (tilts) ϕ of a plurality of transducers with pieces of tomographic image data, as shown in FIG. 3(a). A first frame number in scanning in a direction A is set to "1" and that a last frame number is set to "n." A piece of tomographic image data with a frame number of "1" is first stored in a two-dimensional tomographic image storage unit 9, and a piece of tomographic image data with a frame number of "2" is then stored in the two-dimensional tomographic image storage unit 9. Finally, a piece of tomographic image data with a frame number of "n" is stored in the two-dimensional tomographic image storage unit 9. Also, a first frame number in scanning in a direction B is set to "n" and that a last frame number is set to "1." Pieces of tomographic image data are stored in the two-dimensional tomographic image storage unit 9.

In the meantime, a displacement measurement unit 30, an elasticity information calculation unit 32, and an elasticity image construction unit 34 construct elasticity images 202 with frame number of Fn.0 to Fn.n−1 on the basis the pieces 201 of tomographic image data with the frame numbers of Fr.0 to Fr.n obtained at the adjoining frame intervals A. The elasticity images 202 with the frame numbers of Fn.0 to Fn.n−1 are stored in a two-dimensional elasticity image storage unit 39 and are converted into volume data by an elasticity volume data generating unit 40. Since coordinates of each elasticity image 202 of the volume data are in a polar coordinate system using the swing angle ϕ, the coordinates are converted into X, Y, and Z coordinates by an elasticity three-dimensional scan conversion unit 41. A three-dimensional elasticity image is generated as a projection image by, e.g., surface rendering, the MIP (Max. Impressive) method, or the mIP (minimum Impressive) method in an elasticity volume rendering unit 42.

FIG. 4 illustrate an example in which a phantom three-dimensional elasticity image is constructed using elasticity image measurement according to the present invention. FIG. 4(a) shows how elasticity volume data of a lesioned part 100 is measured by a measurement method according to the first embodiment. The frame interval $\Delta\phi$ for RF signal frame data is about 0.1 mm. In a process in which a deformation of up to about 20 mm (a maximum deformation amount) is caused in an object 1, a plurality of pieces of RF signal frame data were measured during one swing period. As shown in FIG. 4(b), a rendering image of a surface three-dimensional elasticity image as seen from the left front in FIG. 4(a) can be displayed by rendering processing based on elasticity volume data obtained from the plurality of pieces of RF signal frame data.

More specifically, according to the first embodiment, a cross-sectional position is varied while pressing force applied to the surface of the body of the object 1 by the ultrasonic probe 2 of the mechanical 3D probe being in contact with the surface is increased or reduced and the ultrasonic probe 2 is swung. A correlation between two temporally adjoining pieces of RF signal frame data acquired through the swing is obtained, and a displacement of a living tissue at each cross-sectional position is obtained. Pieces of elasticity information of the living tissue at the respective cross-sectional positions are obtained on the basis of pieces of displacement frame data, and elasticity images are sequentially constructed. In other words, a feature of the first embodiment lies in that the two pieces 201 of tomographic image data under different amounts of pressing measured at different cross-sectional positions are measured, that a displacement of the living tissue at either one of the cross-sectional positions or at the average position of the two cross-sectional positions, and that the elasticity images 202 are sequentially constructed. Accordingly, compared with a conventional method, the number of RF signal frame data measurements can be reduced by at least one-half, and the time required to measure elasticity image volume data can be reduced by at least one-half. That is, a conventional method that measures two pieces of tomographic image data under different amounts of pressing at a single cross-sectional position to obtain a displacement of a living tissue at the single cross-sectional position requires a measurement time twice longer than that of the first embodiment.

Also, according to the first embodiment, since one measured latest of two pieces of RF signal frame data used for displacement measurement need not be stored in a memory, the memory capacity of an RF signal frame data selection unit 28 can be reduced.

Note that, according to the first embodiment, since two pieces of RF signal frame data for obtaining a displacement of a living tissue are measured at different scan planes, the accuracy of displacement data of a living tissue is lower than a conventional technique. However, since RF signal frame data is periodically measured, a change in the amount of pressing from one piece of RF signal frame data to another and a change from one scan plane to another are continuous. Additionally, since the period of measurement of RF signal frame data is much shorter than the time for a scan plane to change, a plurality of pieces of displacement frame data, for which the degree of uniformity in the magnitudes of the amounts of pressing and the difference between the amounts of pressing is allowable, can be measured. As a result, a plurality of elasticity images, for which the degree of uniformity in the magnitudes of the amounts of pressing and the difference between the amounts of pressing is allowable, can be constructed.

Since elasticity information is obtained especially on the basis of a displacement of a living tissue between two pieces of tomographic image data next to each other in measurement time, a positional shift of a living tissue caused by the difference in scan plane can be reduced to be negligible. For example, scan planes in a short axis direction for measurement by the ultrasonic probe 2 are generally placed at intervals of, e.g., 0.05 to 0.1 mm, although the interval depends on the frame rate. The pieces 201 of tomographic image data are measured by swinging or linearly moving the ultrasonic probe 2. On the other hand, an ultrasonic beam diameter is about 1 mm, and most of a living tissue is redundantly measured in the pieces 201 of tomographic image data at adjoining scan planes. Accordingly, a positional shift of the living tissue included in the measured pieces 201 of tomographic image data is almost negligible in spite of different scan planes. In light of this, the two pieces 201 of tomographic image data to be selected are not limited to ones at two adjoining scan planes. The two pieces 201 of tomographic image data can be selected from among the pieces 201 of tomographic image data, between which a difference in measurement time falls within a range set such that the diameters of ultrasonic reception beams of reflection echo signals at a plurality of adjacent scan planes overlap with each other.

Note that if measurement is performed while the ultrasonic probe 2 is swung on a circular arc with a radius of, e.g., 80 mm, the interval between the adjoining pieces 201 of tomographic image data to be measured increases with an increase in depth. It is thus preferable that a frame interval $\Delta\phi$ is corrected according to depth in displacement calculation. However, even without correction, an error is negligibly small.

Second Embodiment

A processing procedure according to the second embodiment of elasticity image measurement will be described with reference to FIG. 5. The second embodiment is different from the first embodiment in that a displacement is detected not by the process of performing correlation calculation between adjoining frames but by performing correlation calculation between ones selected from among a plurality of adjacent frames, between which a difference in measurement time falls within a range set such that the diameters of ultrasonic reception beams overlap with each other, while swinging an ultrasonic probe 2 in a short axis direction. For example, as shown in FIG. 5(a), pieces 201 of tomographic image data of four frames Nos. Fr.0 to Fr.3 corresponding to four scan planes adjoining to each other in a scan direction are measured. For example, the two pieces 201 of tomographic image data of the frames Nos. Fr.0 and Fr.2 or Fr.3 are selected from among the pieces 201 of tomographic image data, and one elasticity image 204 is constructed.

A selection criterion for selecting two from among the plurality of pieces 201 of tomographic image data can be arbitrarily set by inputting a parameter such as a frame interval (or swing interval) $\Delta\phi$ from a user interface unit 43. For example, as shown in FIG. 5(b), $\Delta\phi1, \Delta\phi2, \Delta\phi3, \ldots$ satisfying $\Delta\phi1<\Delta\phi2<\Delta\phi3 \ldots$ can be set as the swing angle intervals $\Delta\phi$. For the set intervals $\Delta\phi$, a displacement measurement unit 30 selects a past piece of tomographic image data (e.g., Fr.0 or Fr.2) measured earlier by $\Delta\phi$ than a piece of tomographic image data measured latest (e.g., Fr.3) and calculates a piece of displacement frame data on the basis of the two pieces of tomographic image data.

The selection criterion is not limited to the method in FIG. 5(b). As for the selection criterion for selecting two from among the plurality of pieces 201 of tomographic image data, a correlation between the latest piece 201 of tomographic image data as a reference and a piece of RF signal frame data of each of the plurality of frames Nos. Fr.0 to Fr.3, ... may be obtained, a piece of displacement frame data may be calculated between the piece 201 of tomographic image data as the reference and the piece 201 of tomographic image data having a highest correlation therewith, and an elasticity image may be constructed.

According to the second embodiment, one elasticity image is constructed from the pieces 201 of tomographic image data measured at a plurality of scan planes. Accordingly, the time required for displacement measurement, elasticity information calculation, and elasticity image construction can be significantly shortened, and the number of pieces of elasticity image data constituting elasticity volume data can be reduced. This allows shortening of the time required for volume rendering, high-speed construction of a three-dimensional elasticity image, and an increase in immediacy.

Third Embodiment

A processing procedure according to the third embodiment of elasticity image measurement will be described with reference to FIG. 6. The third embodiment is different from the first embodiment in that RF signal frame data is measured by an ultrasonic probe 2 whose swing speed is set to be lower at two ends of a swing range. More specifically, since a scan plane for transmitting/receiving ultrasonic waves is swung in a fan-shaped manner, frame intervals $\Delta\phi 1$ and $\Delta\phi 3$ at the two ends of the swing range are wider than a frame interval $\Delta\phi 2$ at the center of the swing range, as shown in FIG. 6(a). The distance between adjoining frames at each end of the swing range is long especially at a deeper depth. Also, a deviation of an angle of transmission/reception of ultrasonic waves with respect to a pressing direction increases, and the resolution decreases. For this reason, as shown in FIG. 6(b), a feature of the third embodiment lies in that the swing speed decreases from the center of the swing range toward the two ends, that the frame interval between pieces of RF signal frame data measured at the center is widened, and that the frame intervals at the two ends are narrowed so as to obtain a piece of RF signal frame data at short intervals. In order to implement the third embodiment, a swing speed pattern to be set is supplied from an interface unit 43 to a motor control unit 46c.

In other words, according to the third embodiment, a frame interval is controlled according to a swing position (swing angle) in a short axis direction. The third embodiment is adapted such that the frame interval can be set to decrease with an increase in a deviation of an angle of wave transmission with respect to the pressing direction. A slighter deviation in a short axis direction is preferable in order to accurately measure a displacement of a pixel of each elasticity image at the time of constructing the elasticity image. The accuracy increases with a decrease in deviation. On the other hand, a higher swing speed is preferable from the viewpoint of simplicity and speedup. In this regard, according to the third embodiment, the swing speed is reduced outside the swing range where a deviation of a scan plane is large to accurately acquire pieces of RF signal frame data, and the swing speed is controlled to be high at the center where a deviation of a scan plane is small. This can achieve both high accuracy and high speed.

That is, according to the third embodiment, it is possible to uniformize the resolutions of elasticity images measured within a swing range and shorten the time required to measure elasticity images.

Fourth Embodiment

A processing procedure according to the fourth embodiment of elasticity image measurement will be described with reference to FIG. 7. The fourth embodiment is different from the first embodiment in that a range in a depth direction is divided into a plurality of (two in FIG. 7) depth sections and that the swing speed of an ultrasonic probe 2 is controlled according to a depth in each depth section. More specifically, as shown in FIG. 7(a), a shallow depth section 502 and a deeper depth section 503 are set. As shown in FIG. 7(b), the speed of a motor 46b of a mechanical 3D probe is controlled so as to widen a frame interval $\Delta\phi 1$ for the shallow depth section 502 and narrow a frame interval $\Delta\phi 2$ for the deep depth section 503. That is, general mechanical 3D probes which mechanically swing the ultrasonic probe 2 often move the ultrasonic probe 2 by a swing from the central axis of a swing range. In this case, the distance (time difference) between frames is short for elasticity images at a shallow depth from the ultrasonic probe 2, and the distance between frames is long at a deep depth. For this reason, in the fourth embodiment, the swing speed is reduced so as to reduce the distance between frames when an elasticity image of a deep part is to be obtained. The swing speed is controlled to be high so as to increase the distance between frames when an elasticity image of a shallow part is to be obtained.

In the case of the fourth embodiment, the ultrasonic probe 2 reciprocates or swings twice for each of the depth sections 502 and 503 to measure elasticity images for the sections. That is, an elasticity image construction unit 34 constructs an elasticity image on the basis of pieces 201 of tomographic image data measured for each depth section. In the fourth embodiment, the resolution of a part of interest desired to be observed in a three-dimensional elasticity image can be increased by controlling the swing speed so as to narrow a frame interval $\Delta\phi$ for a depth section including the part of interest.

Fifth Embodiment

Figure 8:
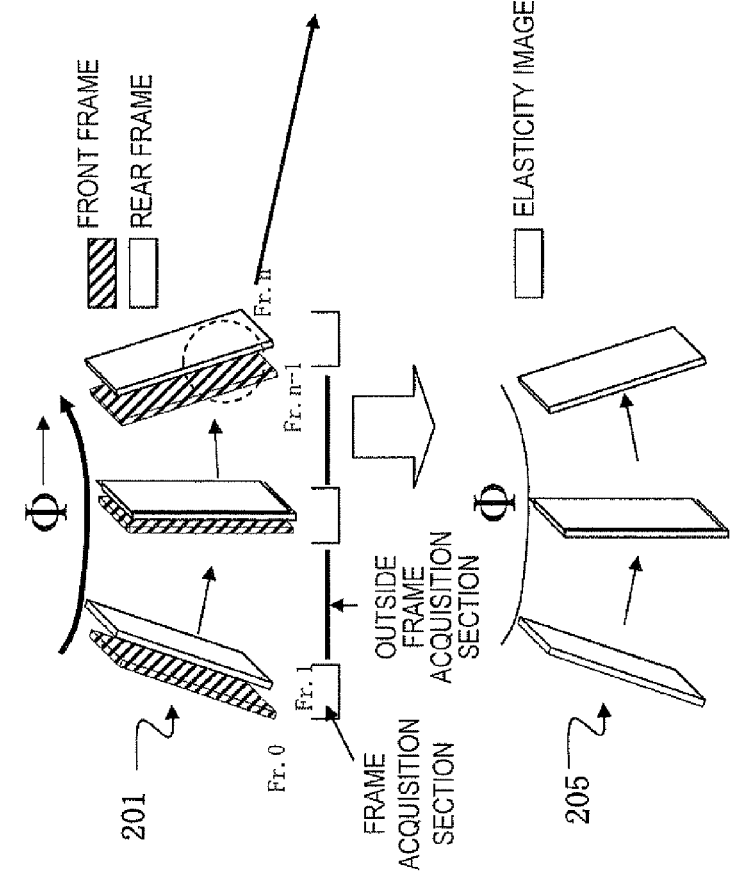
FIG. 8 are figures for explaining elasticity image measurement according to a fifth embodiment of the present invention.

A processing procedure according to the fifth embodiment of elasticity image measurement will be described with reference to FIG. 8. The fifth embodiment is different from the first embodiment in that the swing speed of an ultrasonic probe 2 is periodically controlled to increase and decrease and that an elasticity image construction unit 34 constructs an elasticity image on the basis of pieces of RF signal frame data measured in a swing section where the swing speed is low. More specifically, as shown in FIG. 8(b), a motor control unit 46c of a mechanical 3D probe divides a swing range into a section 603 outside a frame acquisition section for frames of pieces 201 of tomographic image data and a section 604 at the time of frame acquisition and periodically controls the swing speed to increase and decrease such that the swing speed is low at or near the section 604 at the time of frame acquisition and is high in the section 603 outside a frame acquisition section.

In accordance with the control, a displacement measurement unit 30 obtains a piece of displacement frame data on the basis of the two pieces 201 of tomographic image data measured at the time of frame acquisition in the section 604 when the swing speed is low. The elasticity image construction unit 34 constructs an elasticity image 205 on the basis of the piece of displacement frame data. That is, the elasticity image 205 is constructed on the basis of a piece of displacement frame data measured when the swing speed is low. In other words, construction of the elasticity images 205 from the pieces 201 of tomographic image data left after the plurality of measured pieces 201 of tomographic image data are thinned out significantly shortens the time required for displacement measurement, elasticity information calculation, and elasticity image construction. The cycle of increase and decrease in swing speed in FIG. 8(b) can be arbitrarily and variably set by specification through an interface unit 43.

According to the fifth embodiment, the time required for elasticity image measurement can be significantly shortened, and the number of pieces of elasticity image data constituting elasticity volume data can be reduced. Accordingly, the time required for volume rendering can be shortened to construct a three-dimensional elasticity image at high speed, which allows an increase in immediacy. That is, the time required to construct a three-dimensional elasticity image and display the three-dimensional elasticity image as a projection image on an image display 13 depends on the time required to swing the ultrasonic probe transmitting/receiving ultrasonic waves in a short axis direction and the time required for rendering processing that constructs a three-dimensional elasticity image. Accordingly, the time required for a swing can be shortened by acquiring the pieces 201 of tomographic image data with a low swing speed at short intervals in or near a section at the time of frame acquisition and swinging the ultrasonic probe at high speed in other sections, as described in the fifth embodiment.

An elasticity image with few artifacts can be constructed by constructing a plurality of elasticity images on the basis of the pieces 201 of tomographic image data acquired with a low speed at short intervals and further merging the plurality of elasticity images. As a result, the number of elasticity images 205 after thinning is small, and rendering processing based on volume data of the elasticity images 205 with few artifacts can also shorten the time required for the rendering processing.

Sixth Embodiment

Figure 9:
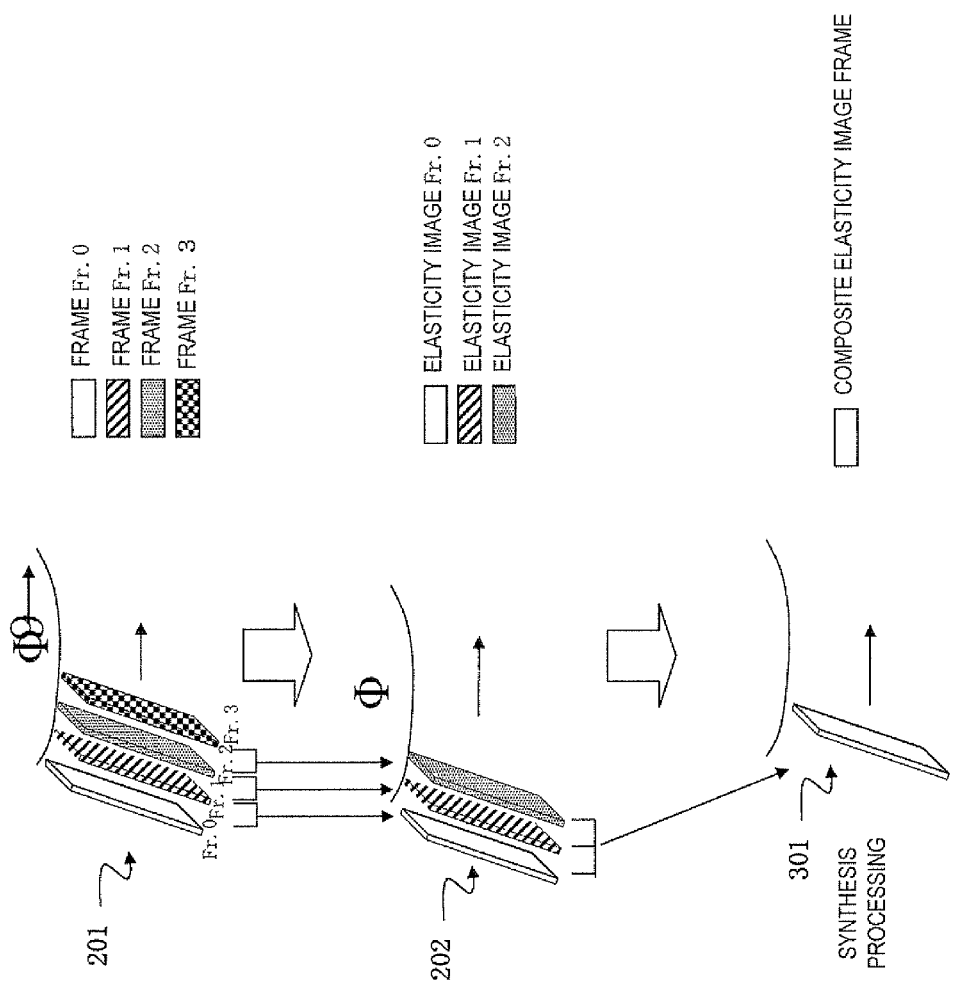
FIG. 9 is a view for explaining elasticity image measurement according to a sixth embodiment of the present invention.

A processing procedure according to the sixth embodiment of elasticity image measurement will be described with reference to FIG. 9. The sixth embodiment is different from the first embodiment in that a plurality of elasticity images 202 constructed on the basis of a plurality of pieces 201 of tomographic image data according to the first embodiment are merged into one elasticity image 301 to reduce artifacts and that rendering is speeded up by reducing volume data. That is, rendering processing is desirably performed on elasticity volume data with reduced artifacts in order to perform clear rendering when a three-dimensional elasticity image is constructed. This is because since rendering processing is performed according to Expressions 4, an image desired to be actually displayed may be displayed with a lower weight in the presence of artifacts in a view direction. In order to reduce such artifacts, as shown in FIG. 9, elasticity volume data is created from the elasticity images 301, each of which is obtained by merging pieces of frame data of the plurality of elasticity images 202 using a method such as addition, averaging, or weighted averaging. This reduces artifacts. Since the synthesis reduces the number of elasticity images 301, the number of elasticity images constituting elasticity volume data can be reduced. For this reason, the calculation time required for rendering processing is reduced, and a three-dimensional elasticity image can be displayed at high speed.

$$\alpha\text{out}i = \alpha\text{in}i + (1-\alpha\text{in}i)\alpha i + \beta i$$

$$E\text{out}i = E\text{in}i + \alpha i^*(1-\alpha\text{in}i)^*Ei \quad \text{(Expressions 4)}$$

More specifically, as shown in FIG. 9(a), a feature of the sixth embodiment lies in that the plurality of elasticity images 202 are constructed on the basis of the two adjoining pieces 201 of tomographic image data measured in the same manner as in the first embodiment and that the plurality of constructed elasticity images 202 are merged into the one elasticity image 301. That is, an elasticity volume data generating unit 40 merges the plurality of elasticity images 202 sequentially constructed by an elasticity image construction unit 34 and stored in a two-dimensional elasticity image storage unit 39 into the one elasticity image 301. The elasticity volume data generating unit 40 sequentially registers each elasticity image 301 after the merging in a memory in association with the average swing angle of a plurality of scan planes corresponding to the plurality of elasticity images. Note that the number of frames of the elasticity images 202 to be merged can be arbitrarily set or switched as a parameter by a user through an interface unit 43.

According to the sixth embodiment, since a plurality of two-dimensional elasticity images can be synthesized into one two-dimensional elasticity image and be averaged, artifacts can be reduced, and volume data can be reduced, which allows speedup of rendering. Note that an elasticity image can be synthesized by any one of addition, averaging, and weighted averaging of a plurality of elasticity images.

Seventh Embodiment

Figure 10:
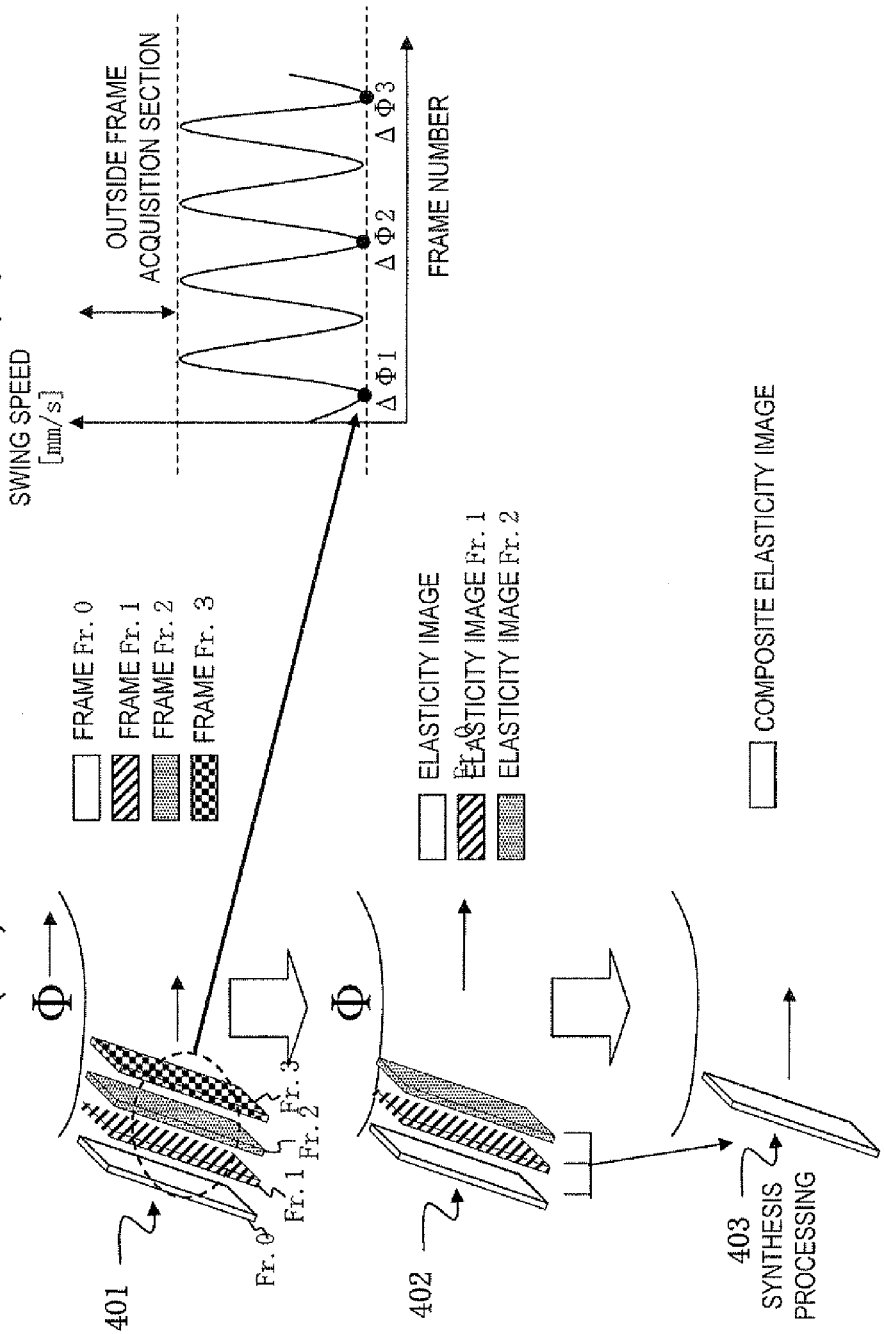
FIG. 10 are figures for explaining elasticity image measurement according to a seventh embodiment of the present invention.

A processing procedure according to the seventh embodiment of elasticity image measurement will be described with reference to FIG. 10. The seventh embodiment is a combination of the fifth and sixth embodiments. More specifically, the swing speed of an ultrasonic probe 2 is periodically controlled to increase and decrease, and an elasticity image construction unit 34 constructs an elasticity image 402 on the basis of pieces 401 of tomographic image data measured in a swing section where the swing speed is low. An elasticity volume data generating unit 40 merges a plurality of elasticity images 402 sequentially constructed by the elasticity image construction unit 34 and stored in a two-dimensional elasticity image storage unit 39 into one elasticity image 403. The elasticity volume data generating unit 40 sequentially registers each elasticity image 403 after the merging in a memory in association with the average swing angle of a plurality of cross-sectional positions corresponding to the plurality of elasticity images.

The time required to construct a three-dimensional elasticity image and display the three-dimensional elasticity image as a projection image on an image display 13 depends on the time required to swing the ultrasonic probe transmitting/receiving ultrasonic waves in a short axis direction and the time required for rendering processing that constructs a three-dimensional elasticity image. Accordingly, like the seventh embodiment, the time required for a swing can be shortened by acquiring the pieces 401 of tomographic image data with a low swing speed at short intervals in or near a section at the time of frame acquisition and swinging the ultrasonic probe at high speed in other sections. Also, the elasticity image 403 with few artifacts can be constructed by constructing the plurality of elasticity images 402 on the basis of the pieces 401 of tomographic image data acquired with a low speed at short intervals and further merging the plurality of elasticity images 402. As a result, the number of elasticity images after thinning is small, and rendering processing based on volume data of the elasticity images 403 with few artifacts can shorten the time required for rendering processing.

Therefore, according to the seventh embodiment, artifacts can be reduced, and volume data can be reduced, which allows further speedup of rendering.

Eighth Embodiment

A processing procedure according to the eighth embodiment of elasticity image measurement will be described with reference to FIG. 11. The eighth embodiment is different from the first embodiment in that an elasticity image and elasticity volume data of only a part of interest and its surroundings desired to be observed in an elasticity image are acquired. More specifically, swing scanning for acquiring elasticity volume data is performed in two steps. As shown in FIG. 11(a), in a first swing scan in a short axis direction, pieces 201 of tomographic image data in a wide area are measured to display tomographic images. If a part 501 of interest such as a tumor is found in the tomographic images obtained by the first swing scan, only a specific swing section including the part 501 of interest and a region therearound is objected to swing scanning in a second swing scan in the short axis direction, as shown in FIG. 11(b). Like the first embodiment, elasticity images for elasticity volume data are acquired.

The part 501 of interest or the specific swing section can be manually set according to a user's determination or can be automatically set. In the case of manual setting, the part 501 of interest is observed while elasticity images acquired in FIG. 11(a) are consecutively displayed, the range for a swing angle φ is determined for the specific swing section including the part 501 of interest, and the range is input and set from an interface unit 43 to a motor control unit 46c. The swing speed in the specific swing section can be variably set. For example, the swing speed can be set in advance in the motor control unit 46c or can be input and set from the interface unit 43 to the motor control unit 46c. The motor control unit 46c controls the swing speed of an ultrasonic probe according to the variably set swing speed in the input specific swing section.

An example in which the part 501 of interest or the specific swing section is automatically set will now be described. For example, at the time of the swing scan in FIG. 11(b), variations in pieces of data in each piece of two-dimensional elasticity frame data obtained by an elasticity information calculation unit 32 are evaluated, and whether the part 501 of interest is included in the piece of elasticity frame data is determined. If the variability of pieces of data in one of the pieces of elasticity frame data is more than a threshold value, the piece of elasticity frame data is determined to include the part 501 of interest. The determination processing is continued in a swing direction, and the part 501 of interest is automatically detected. While the part 501 of interest is detected, an elasticity image is constructed with a low swing speed. If the part 501 of interest is not detected, the swing speed is set to a high speed, and elasticity image construction is suspended. Note that a section with wide variations in deviations σ or variances of pieces of data in a piece of elasticity frame data shown in Expression 5 below and FIG. 11(b) may be detected at the time of determination of variations in pieces of data of a piece of elasticity frame data.

$$\sigma = \sqrt{\frac{1}{n}\sum_{i=1}^{n}(\varepsilon i - \overline{\varepsilon})}$$ (Expression 5)

where σ is a deviation, εi is one piece of data in a frame, and $\overline{\varepsilon}$ is an average in a frame.

That is, in the eighth embodiment, a part-of-interest detection unit which detects, on the basis of elasticity frame data and in light of preset conditions, whether the part 501 of interest desired to be observed in a three-dimensional elasticity image is included is provided in the elasticity information calculation unit 32. The motor control unit 46c of an ultrasonic probe swing device 46 controls the swing speed of an ultrasonic probe 2 to be low within a swing angle range corresponding to the specific swing section, in response to a signal indicating detection of the part 501 of interest output from the part-of-interest detection unit of the elasticity information calculation unit 32.

According to the eighth embodiment, since the time required to measure an elasticity image outside a region including the part 501 of interest can be shortened, and the number of elasticity images to be rendered is reduced, it is possible to shorten the time required to project a three-dimensional elasticity image while maintaining the resolution of an elasticity image of a region including the part 501 of interest. This allows shortening of the time required for generation of elasticity volume data and rendering. Accordingly, the immediacy increases, and the size of a memory for storing elasticity volume data can be reduced.

The eighth embodiment has described an example in which scanning for acquiring elasticity volume data is performed in two steps. The number of steps, however, is not limited to 2, and the scanning can be performed in a plurality of steps. That is, transmission/reception of ultrasonic waves measuring the pieces 201 of tomographic image data at a plurality of scan planes by an ultrasonic wave transmission/reception unit is performed a plurality of times. The elasticity image construction unit 34 includes a part-of-interest detection unit that detects the part 501 of interest meeting preset conditions on the basis of tomographic images obtained by initial measurement of the pieces 201 of tomographic image data. After the part-of-interest detection unit detects the part 501 of interest, the motor control unit 46c switches the swing speed of the ultrasonic probe 2 at a plurality of scan planes including the part 501 of interest to a low speed at the time of measurement of the pieces 201 of tomographic image data. The elasticity image construction unit 34 constructs an elasticity image on the basis of the pieces 201 of tomographic image data measured at a plurality of cross-sectional positions including the part 501 of interest within the swing range of the ultrasonic probe 2.

Ninth Embodiment

A processing procedure according to the ninth embodiment of elasticity image measurement will be described with reference to FIG. 12. The ninth embodiment is different from the eighth embodiment in that the speed of swing is low in a specific swing section 601 corresponding to a plurality of scan planes including a part 501 of interest desired to be observed in a three-dimensional elasticity image, as shown in FIG. 12(b), and that the speed of swing is high in other sections 602. Methods for setting and detecting the specific swing section 601 are the same as those in the eighth embodiment. That is, a motor control unit of an ultrasonic probe swing device 46 controls the swing speed of an ultrasonic probe to be low according to a variably set swing speed in the input specific swing section 601 and controls the swing speed of the ultrasonic probe to be high in the other sections 602.

According to the ninth embodiment, setting of the swing speed to a low speed in a frame acquisition section allows frame acquisition at reduced speed at short intervals in an important section. More specifically, in the specific swing section 601 including the part 501 of interest desired to be observed in a three-dimensional elasticity image, the interval of frames is short, and pieces 201 of tomographic image data are measured at short intervals. Elasticity volume data is acquired in the same manner as in the first embodiment. Although high-speed swinging in an unnecessary part degrades the image quality of an obtained elasticity image, the whole of the image can be grasped. The viewing angle at the time of rendering is wide, and an important part can be displayed in a high-definition three-dimensional elasticity image.

On the other hand, high-speed swinging in the swing sections 602 not including the part 501 of interest degrades the image quality of an elasticity image. However, since the time required for generation of elasticity volume data and rendering can be shortened on the whole, the immediacy increases, and the size of a memory for storing elasticity volume data can be reduced.

Tenth Embodiment

Figure 13:
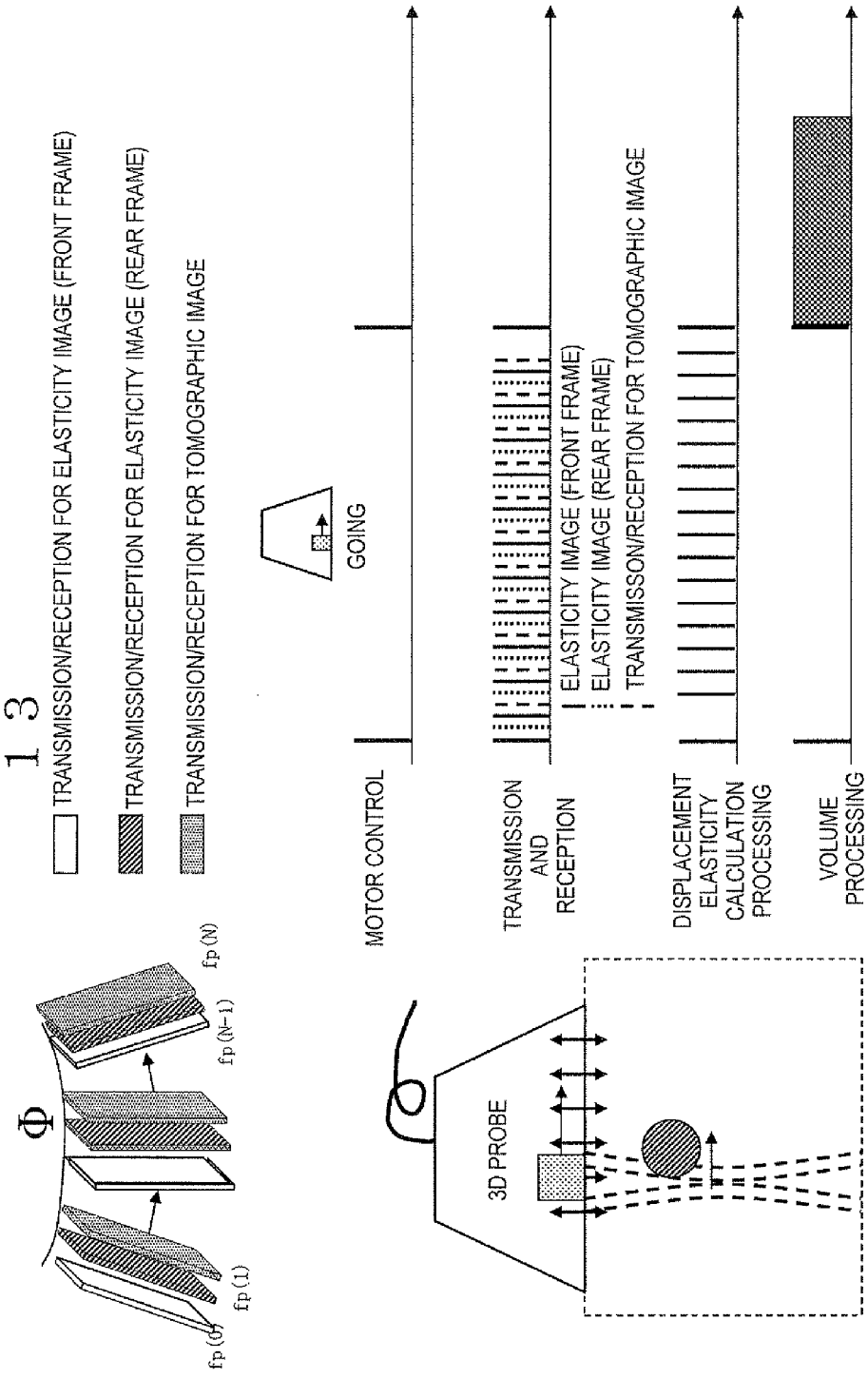
FIG. 13 are figures for explaining elasticity image measurement according to a tenth embodiment of the present invention.

A processing procedure according to the tenth embodiment of elasticity image measurement will be described with reference to FIG. 13. The tenth embodiment is different from the first embodiment or the other embodiments in that patterns (e.g., frequency, pulse pattern, and intensity) of ultrasonic waves for elasticity image acquisition and for tomographic image acquisition can be made different. More specifically, as shown in FIG. 13(a), in a process in which pressing force applied to an object by an ultrasonic probe is changed and a scan plane for transmitting/receiving ultrasonic waves to/from the object is moved in a short axis direction indicated by arrows, ultrasonic waves are periodically transmitted/received to/from the object, and RF signal frame data is consecutively measured. In the present embodiment, in particular, preset ultrasonic waves for elasticity image acquisition and preset ultrasonic waves for tomographic image acquisition as a set are repeatedly transmitted to a plurality of (two in the illustrated example) consecutive scan planes and one subsequent scan plane, respectively. In response to this, a reception unit 4 and a phasing addition unit 6 generate and output a set of three pieces of RF signal frame data.

As shown in FIG. 13(c), in a process in which a mechanical 3D probe is swung in one direction, two pieces of RF signal frame data for an elasticity image (a front frame and a rear frame) and one piece of RF signal frame data for a tomographic image are repeatedly acquired. At this time, since the period of transmission of ultrasonic waves for elasticity image acquisition is set to a period that causes the diameters of ultrasonic reception beams of sequentially received reflection echo signals to overlap with each other, pieces of RF signal frame data are also acquired at intervals that cause the diameters of ultrasonic reception beams to overlap with each other.

A piece of RF signal frame data for a tomographic image acquired in the above-described manner is input to a tomographic image construction unit 7, and a tomographic image is constructed. In the meantime, two pieces of RF signal frame data for an elastic image are input to an elasticity information calculation unit 32 via an RF signal frame data selection unit 28 and a displacement measurement unit 30. For this reason, as shown in FIG. 13(c), elasticity information is calculated, an elasticity image is constructed in an elasticity image construction unit 34 at intervals of the three pieces of RF signal frame data, and a piece of elasticity frame data is generated. When pieces of elasticity frame data are accumulated, an arbitrary 3D elasticity image is generated by volume rendering processing and is displayed on a screen.

According to the tenth embodiment, patterns (e.g., frequency, pulse pattern, and intensity) of ultrasonic waves suitable for elasticity image acquisition and for tomographic image acquisition can be used, and the image quality of an elasticity image, that of a tomographic image, and the like can be improved. Also, the reduction in the number of tomographic images constituting tomographic volume data allows speedup of rendering processing of a three-dimensional tomographic image.

Figure 2:
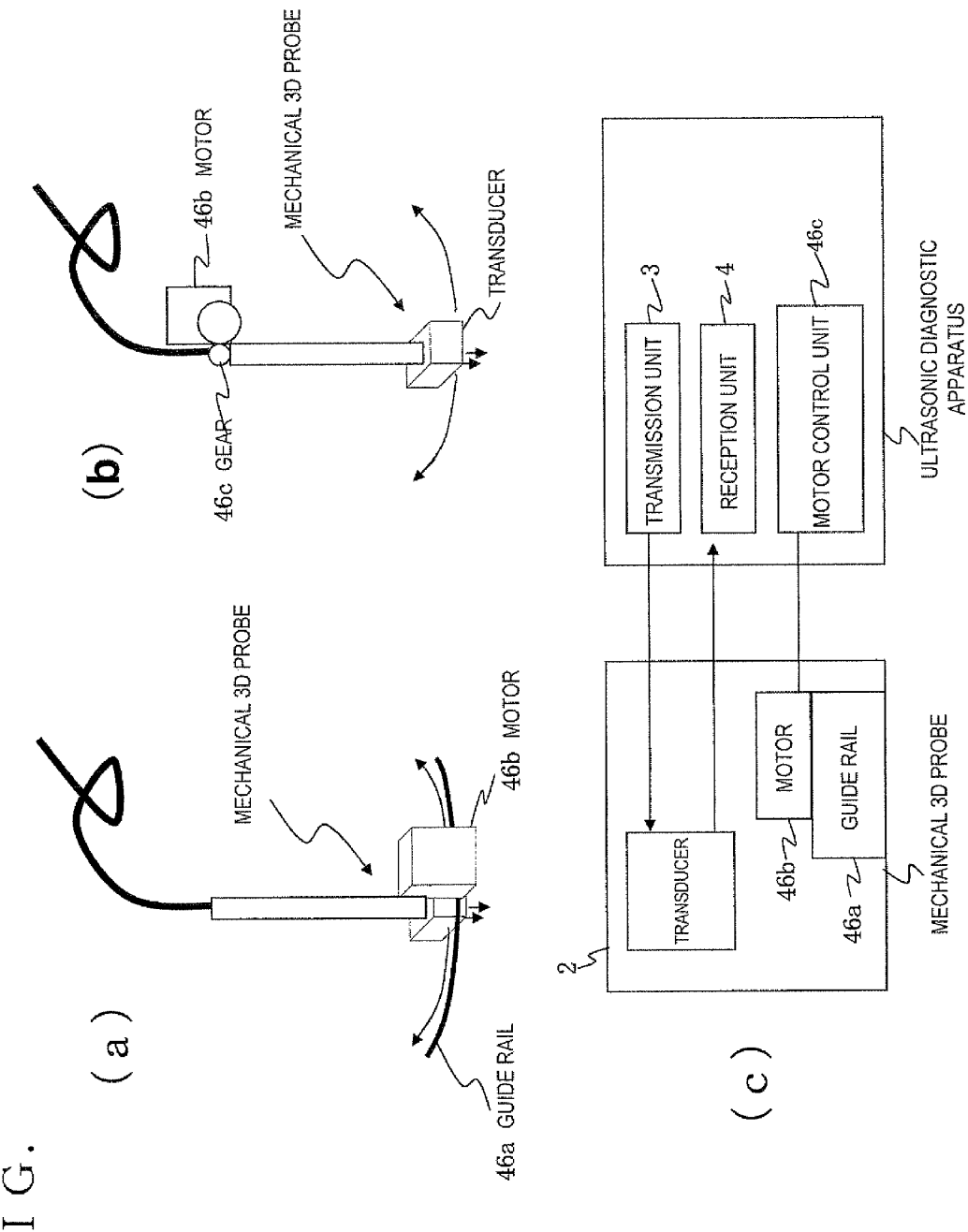
FIG. 2 are figures of an example of a swing device for an ultrasonic probe which is used in elasticity image measurement according to the present invention.

The above first to tenth embodiments have described examples in which movement of the ultrasonic probe 2 in the short axis direction is implemented by an arcuate swing by the mechanical 3D probe shown in FIG. 2. The present invention, however, is not limited to this. More specifically, movement of the ultrasonic probe 2 in the short axis direction may be linear. In this case, the guide rail 46a that guides the ultrasonic probe 2 in FIG. 2 is linearly formed. Alternatively, the ultrasonic probe 2 may be swung or linearly moved in the short axis direction not by mechanical means but by manual operation.

REFERENCE SIGNS LIST 1 object
2 ultrasonic probe
3 transmission unit
4 reception unit
5 transmission/reception control unit
6 phasing addition unit
7 tomographic image construction unit
9 two-dimensional tomographic image storage unit
12 switching synthesis unit
13 image display
28 RF signal frame data selection unit
30 displacement measurement unit
32 elasticity information calculation unit
34 elasticity image construction unit
39 two-dimensional elasticity image storage unit
36 tomographic volume data generating unit
37 tomographic three-dimensional scan conversion unit
38 tomographic volume rendering unit
40 elasticity volume data generating unit
41 elasticity three-dimensional scan conversion unit
42 elasticity volume rendering unit

The invention claimed is:
1. An ultrasonic diagnostic apparatus for use with a living tissue, the ultrasonic diagnostic apparatus comprising:
an ultrasonic probe which transmits ultrasonic waves to an object and receives a reflected echo signal from the object while being in contact with the object; and
an ultrasonic diagnostic system including circuitry, memory and a display, the ultrasonic diagnostic system being programmed to:
transmit periodically the ultrasonic waves to the object through the ultrasonic probe, and receive the reflected echo signal and receive the reflection echo signal from the object through the ultrasonic probe, in a process in which a pressing force applied to the object by the ultrasonic probe is changed and a cross-sectional position to transmit or receive ultrasonic waves to or from the object is continuously moved in a short-axis direction of the ultrasonic probe;
obtain a displacement of the living tissue between two pieces of RF signal frame data selected from among a plurality of pieces of RF signal frame data captured at a plurality of different cross-sectional positions sequentially received by the ultrasonic probe and selected within a set range of a difference in measurement time, and generate sequentially a plurality of displacement frame data;
calculate elasticity information of the living tissue at the cross-sectional position based on the displacement frame data, and generate elasticity frame data sequentially based on the calculated elasticity information; and construct elasticity images sequentially based on the generated elasticity frame data.

2. The ultrasonic diagnostic apparatus according to claim 1, wherein the ultrasonic diagnostic system is programmed to:

store the constructed elastic images in the memory together with respective pieces of positional information of the cross-sectional position; and construct a three-dimensional elasticity image by rendering the volume data of the elasticity images stored in the memory and display the three-dimensional elasticity image on the display.

3. The ultrasonic diagnostic apparatus according to claim 1, wherein a change of the pressing force applied to the object and a movement of the cross-sectional position in the short-axis direction are manually performed while the ultrasonic probe is grasped.

4. The ultrasonic diagnostic apparatus according to claim 1, wherein the ultrasonic probe is assembled to a swing apparatus which arcuately or linearly guides the cross-sectional position to transmit or receive ultrasonic waves.

5. The ultrasonic diagnostic apparatus according to claim 1, wherein:

the ultrasonic probe is formed to include a plurality of two-dimensionally arranged transducers, the ultrasonic diagnostic system is programmed to move the cross-sectional position by electronically scanning the plurality of transducers in the short-axis direction of the ultrasonic probe, and a change of the pressing force applied to the object can be manually performed in response to the ultrasonic probe being grasped.

6. The ultrasonic diagnostic apparatus according to claim 1, further comprising:

a swing device including:
   a swing mechanism which swings the ultrasonic probe in the short-axis direction,
   a motor which swings and drives the ultrasonic probe via the swing mechanism, and
   a motor control unit which senses a swing angle of the ultrasonic probe from a rotational position of the motor and controls a rotational speed of the motor;

wherein the ultrasonic diagnostic system is programmed to:

store the constructed elastic images in the memory in association with respective swing angles of the ultrasonic probe; and construct a three-dimensional elasticity image by rendering the volume data of the elasticity images stored in the memory and display the three-dimensional elasticity image on the display.

7. The ultrasonic diagnostic apparatus according to claim 6, wherein the motor control unit performs at least one of:

first control that controls speed of the motor in a pattern with a swing speed decreasing from a center of a swing range of the ultrasonic probe toward two ends;

second control that controls the swing speed of the ultrasonic probe according to a depth for one of a plurality of depth sections into which a range in a depth direction is divided;

third control that controls the swing speed of the ultrasonic probe according to depth of a part-of-interest desired to be observed in the three-dimensional elasticity image;

fourth control that periodically controls the swing speed of the ultrasonic probe to increase and decrease;

fifth control that controls the swing speed of the ultrasonic probe to be low in a specific swing section corresponding to a plurality of cross-sectional positions including a part-of-interest desired to be observed in the three-dimensional elasticity image and controls the swing speed to be high outside the specific swing section; and sixth control that performs control according to variably set swing speed of the ultrasonic probe in the specific swing section corresponding to the plurality of cross-sectional positions including a part-of-interest desired to be observed in the three-dimensional elasticity image.

8. The ultrasonic diagnostic apparatus according to claim 6, wherein the ultrasonic diagnostic system is programmed to:

detect whether a part-of-interest desired is present in the three-dimensional elasticity image based on the elasticity frame data and a preset condition, and control a swing speed of the ultrasonic probe to be low in response to a signal indicating the presence of the part-of-interest and control the swing speed of the ultrasonic probe to be high in response to a signal indicating the presence of the part-of-interest.

9. The ultrasonic diagnostic apparatus according to claim 6, wherein the ultrasonic diagnostic system is programmed to:

construct a tomographic image based on the RF signal frame data, transmit or receive ultrasonic waves for measuring the RF signal frame data at a plurality of the cross-sectional positions a plurality of times, detect a part-of-interest that meets a preset condition as a part to be observed in the three-dimensional elasticity image based on the tomographic image obtained by initial measurement of the RF signal frame data, switch swing speed of the ultrasonic probe at a plurality of cross-sectional positions including a part-of-interest to a low speed at the time of measurement of the RF signal frame data after part-of-interest is detected, and construct the elasticity images based on the RF signal frame data measured at the plurality of cross-sectional positions including a part-of-interest within a swing range of the ultrasonic probe.

10. The ultrasonic diagnostic apparatus according to claim 6, wherein the ultrasonic diagnostic system is programmed to:

transmit or receive ultrasonic waves to measure the RF signal frame data at a plurality of the cross-sectional positions a plurality of times, detect a part-of-interest that meets a preset condition as a part to be observed in the three-dimensional elasticity image based on the elasticity images obtained by initial measurement of the RF signal frame data, switch the swing speed of the ultrasonic probe at a plurality of cross-sectional positions including a part-of-interest to a low speed at the time of measurement of the RF signal frame data after a part-of-interest is detected, and construct the elasticity images based on the RF signal frame data measured at the plurality of cross-sectional positions including a part-of-interest within a swing range of the ultrasonic probe.

11. The ultrasonic diagnostic apparatus according to claim 1, wherein
the set range of the difference in measurement time between the two pieces of RF signal frame data is selected based on a difference in measurement time that causes diameters of ultrasonic reception beams of the reflection echo signals at a plurality of cross-sectional positions to overlap with each other.

12. The ultrasonic diagnostic apparatus according to claim 11, wherein
the set range for the difference in measurement time between two selected pieces of RF signal frame data is based on:
(i) a difference in measurement time that causes diameters of ultrasonic reception beams of the reflection echo signals at adjoining ones of the cross-sectional positions to overlap with each other; or
(ii) if three or more pieces of RF signal frame data are measured within the set range for the difference in measurement time, obtains a correlation of a latest one of the three or more pieces of RF signal frame data as a reference with each of the other three or more pieces of RF signal frame data measured within the set range is obtained and the displacement frame data between the two pieces of RF signal frame data having a greatest correlation is obtained.

13. The ultrasonic diagnostic apparatus according to claim 12, wherein the ultrasonic diagnostic system is programmed to:
input and set the part-of-interest desired to be observed in the three-dimensional elasticity image if three or more pieces of RF signal frame data are measured within the set range for the difference in measurement time; and
the motor control unit controls swing speed of the ultrasonic probe to be low in the part-of-interest input from the input setting unit and controls the swing speed of the ultrasonic probe to be high outside the part-of-interest.

14. The ultrasonic diagnostic apparatus according to claim 1, wherein the ultrasonic diagnostic system is programmed to:
transmit preset ultrasonic waves for elasticity image acquisition and preset ultrasonic waves for tomographic image acquisition as a set to a plurality of the consecutive cross-sectional positions and one subsequent cross-sectional position, respectively, and a period of transmission of ultrasonic waves for elasticity image acquisition is set to a period that causes diameters of ultrasonic reception beams of sequentially received reflection echo signals to overlap with each other, and
construct a tomographic image based on measured RF signal frame data in response to the ultrasonic waves for tomographic image acquisition.

15. An elasticity image display method for use with a living tissue, the elasticity image display method comprising:
a first step of periodically transmitting ultrasonic waves to the object and receiving a measured reflection echo signal by the ultrasonic probe, in a process in which a pressing force applied to an object by the ultrasonic probe is changed and a cross-sectional position for transmission of ultrasonic waves is continuously moved in a short-axis direction of the ultrasonic probe;
a second step of performing reception processing on the reflection echo signal captured in the first step and periodically measuring RF signal frame data;
a third step of obtaining displacements of the living tissue at a plurality of the cross-sectional positions and sequentially generating pieces of displacement frame data on the basis of two pieces of RF signal frame data, between which a difference in measurement time falls within a set range, selected from among a plurality of pieces of RF signal frame data periodically measured in the second step and selected within a set range of a difference in measurement time;
a fourth step of on the basis of a plurality of the pieces of displacement frame data obtained in the third step, calculating elasticity information of the living tissue at the plurality of cross-sectional positions and sequentially generating elasticity frame data; and
a fifth step of, on the basis of the elasticity frame data sequentially generated in the fourth step, sequentially constructing elasticity images.

* * * * *